(12) United States Patent
Gardner et al.

(10) Patent No.: US 10,966,692 B2
(45) Date of Patent: Apr. 6, 2021

(54) QUICK RELEASE DRIVING TOOL

(71) Applicant: SNPSHOT TRUSTEE LIMITED, Auckland (NZ)

(72) Inventors: Michael Stuart Gardner, Auckland (NZ); Roy Victor Bladen, Auckland (NZ); Rory Bladen, Auckland (NZ)

(73) Assignee: SNPSHOT TRUSTEE LIMITED, Auchland (NZ)

( * ) Notice: Subject to any disclaimer, the term of this patent is extended or adjusted under 35 U.S.C. 154(b) by 295 days.

(21) Appl. No.: 16/083,296

(22) PCT Filed: Feb. 27, 2017

(86) PCT No.: PCT/IB2017/051115
§ 371 (c)(1),
(2) Date: Sep. 7, 2018

(87) PCT Pub. No.: WO2017/153863
PCT Pub. Date: Sep. 14, 2017

(65) Prior Publication Data
US 2019/0029656 A1  Jan. 31, 2019

Related U.S. Application Data

(60) Provisional application No. 62/316,499, filed on Mar. 31, 2016, provisional application No. 62/305,498, filed on Mar. 8, 2016.

(30) Foreign Application Priority Data

Nov. 2, 2016  (NZ) ........................................ 725837

(51) Int. Cl.
*A61B 10/02*   (2006.01)
*A01K 29/00*   (2006.01)
*A61B 10/00*   (2006.01)

(52) U.S. Cl.
CPC .......... *A61B 10/0275* (2013.01); *A01K 29/00* (2013.01); *A61B 10/0233* (2013.01); *A61B 10/0096* (2013.01); *A61B 2010/0208* (2013.01)

(58) Field of Classification Search
CPC ........ A61B 2010/0208; A61B 10/0233; A61B 10/02–0283
See application file for complete search history.

(56) References Cited

U.S. PATENT DOCUMENTS 5,156,160 A   10/1992  Bennett
5,282,476 A   2/1994  Terwilliger
(Continued)

FOREIGN PATENT DOCUMENTS

WO   2014/196877   12/2014
WO   2015/056225   4/2015

OTHER PUBLICATIONS

PCT/IB2017/051115 International Search Report and Written Opinion of the International Searching Authority dated Jun. 29, 2017 (16 pages).

*Primary Examiner* — Thaddeus B Cox
(74) *Attorney, Agent, or Firm* — Michael Best & Friedrich LLP

(57) ABSTRACT

The present invention relates to a quick release apparatus configurable to drive a driven member. The driven member comprises a primary driver which provides or carries a driven member, and that is able to drive the driven member in a first direction to an operative position. The driven member further comprises an actuable secondary driver. The primary and secondary drivers are configurable between a first mode, wherein the secondary driver is able to drive the primary driver in the first direction, and in a second mode which allows the primary driver to be moved away from the (Continued)

operative position independent of the position of the secondary driver under the influence of a bias.

10 Claims, 33 Drawing Sheets

(56) References Cited

U.S. PATENT DOCUMENTS

| | | |
|---|---|---|
| 2008/0064983 A1 | 3/2008 | Stromberg et al. |
| 2011/0295148 A1 | 12/2011 | Destoumieux et al. |
| 2012/0180290 A1* | 7/2012 | Blacklin .................. G01N 1/02 29/428 |
| 2013/0204159 A1 | 8/2013 | Destoumieux et al. |

* cited by examiner

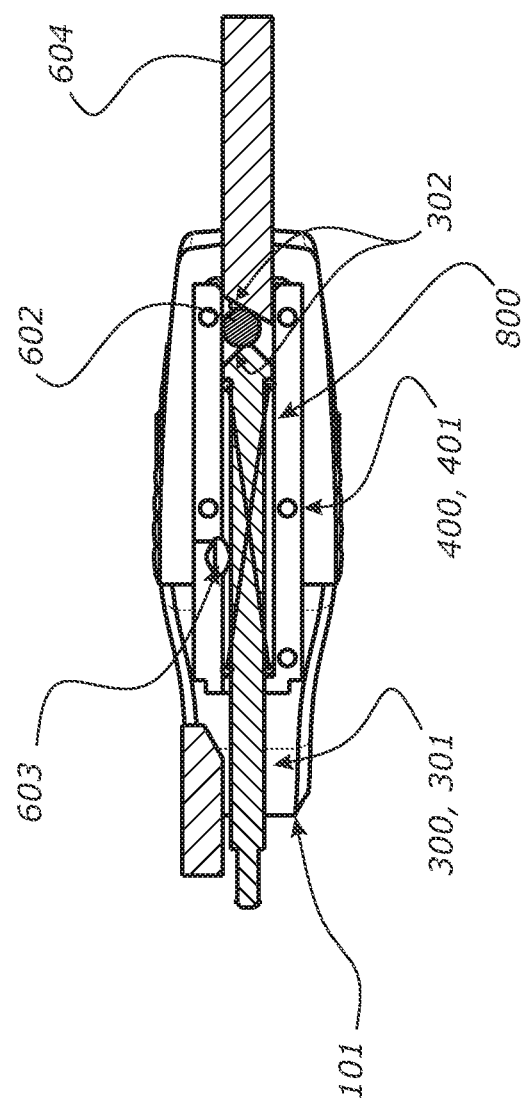
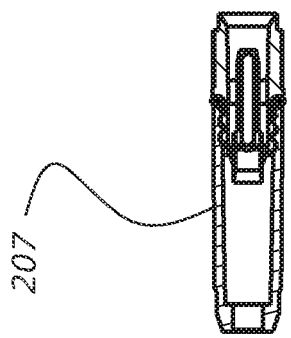
FIGURE 3

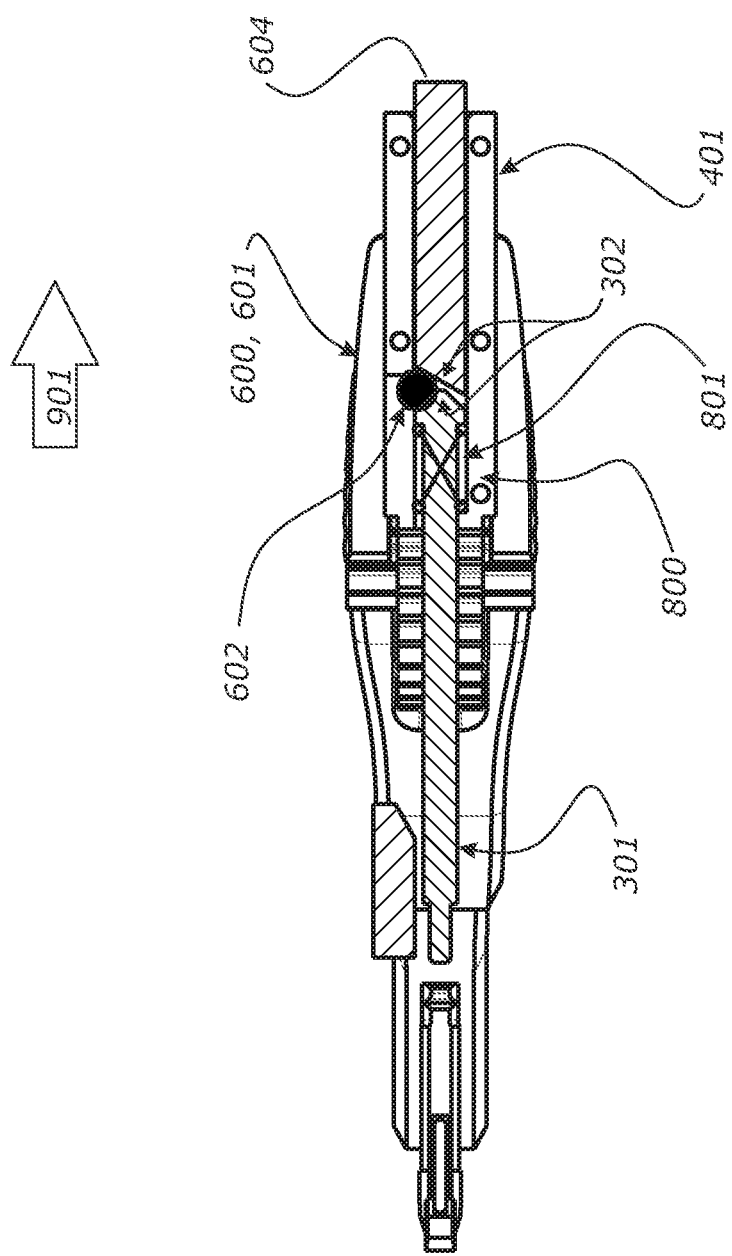
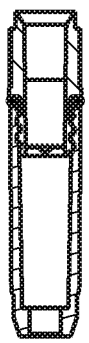
FIGURE 5

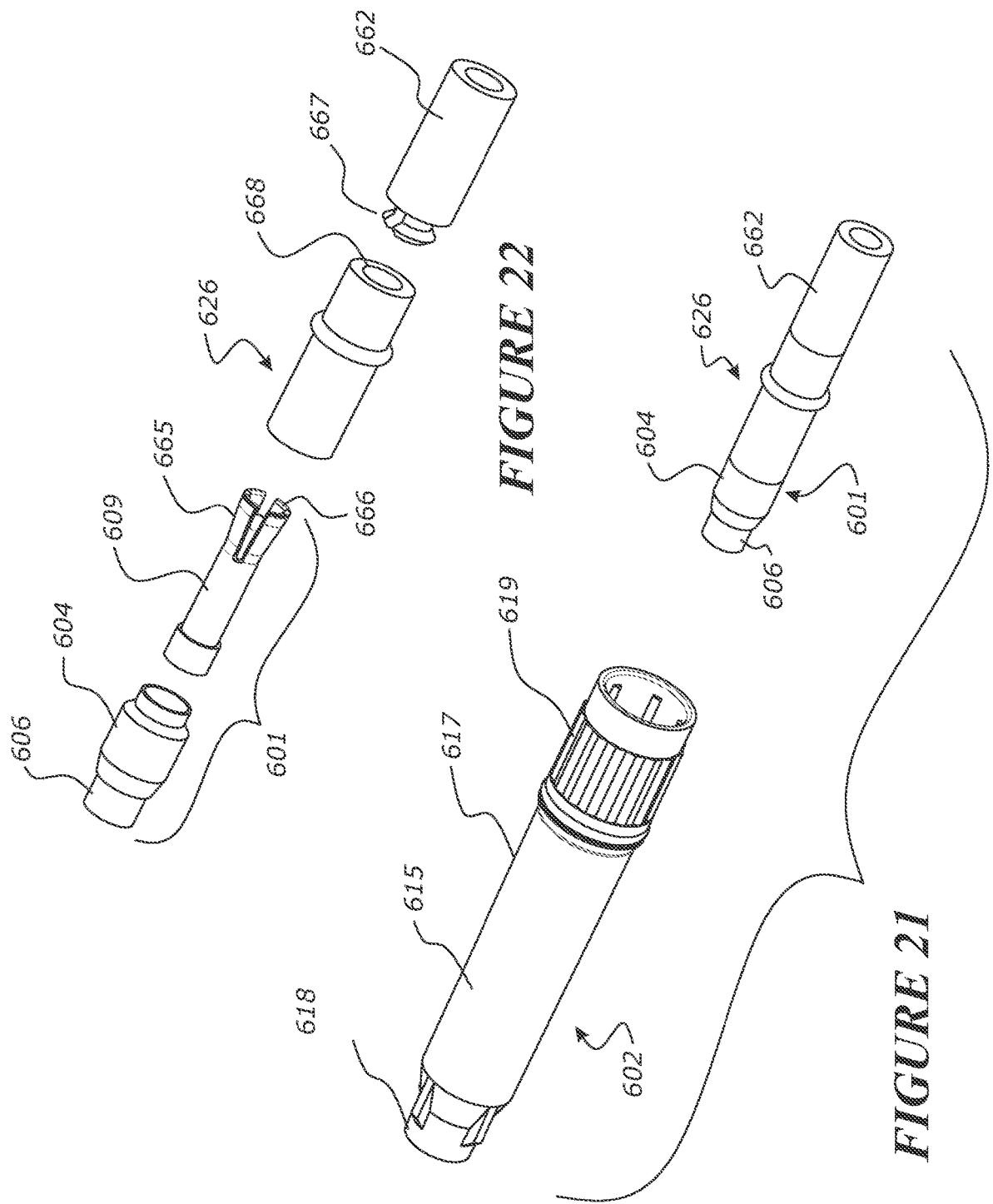

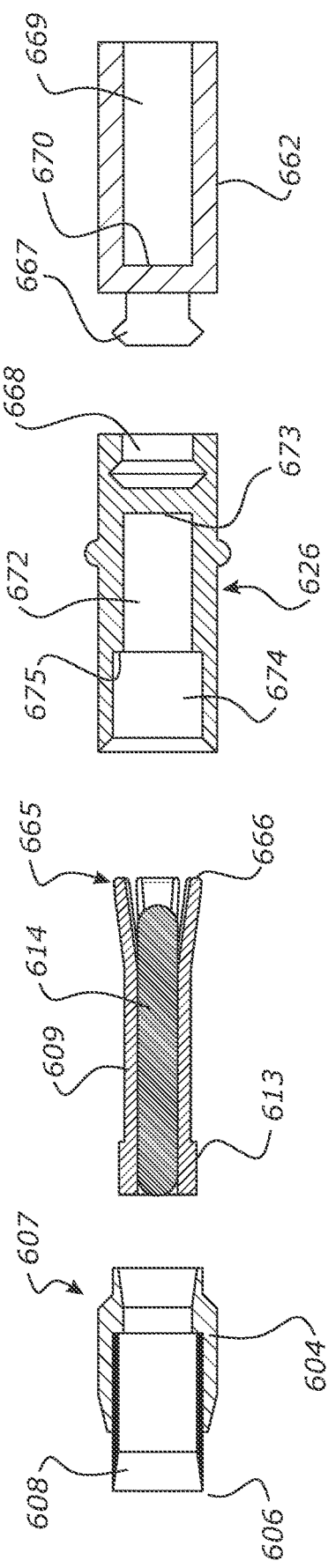
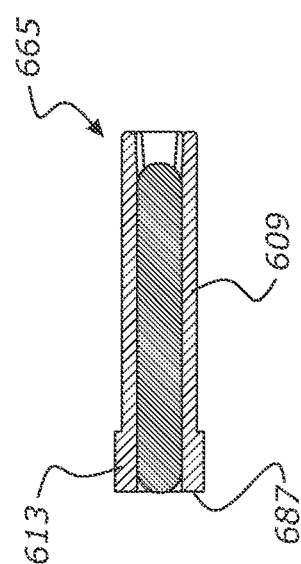
FIGURE 23A
FIGURE 23B

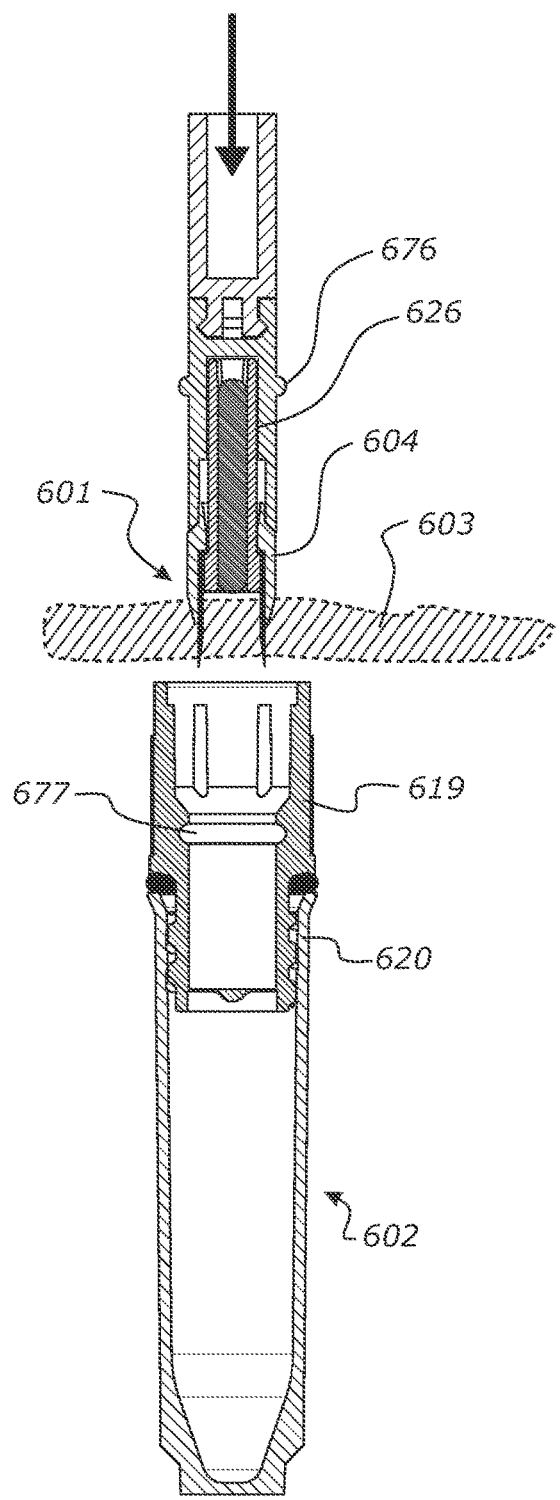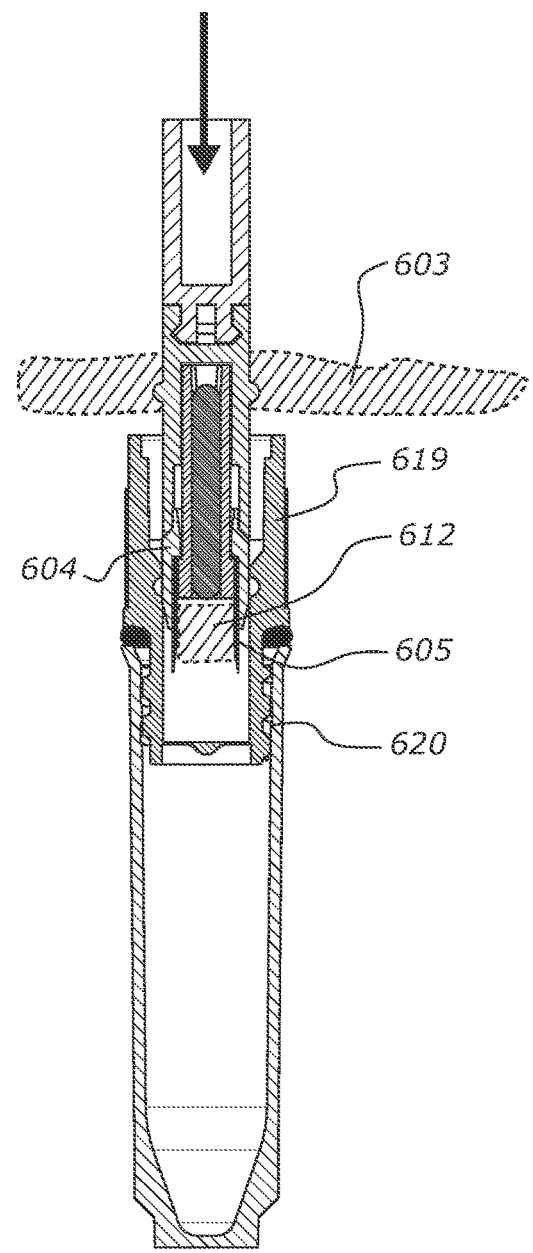
*FIGURE 25*  *FIGURE 26*

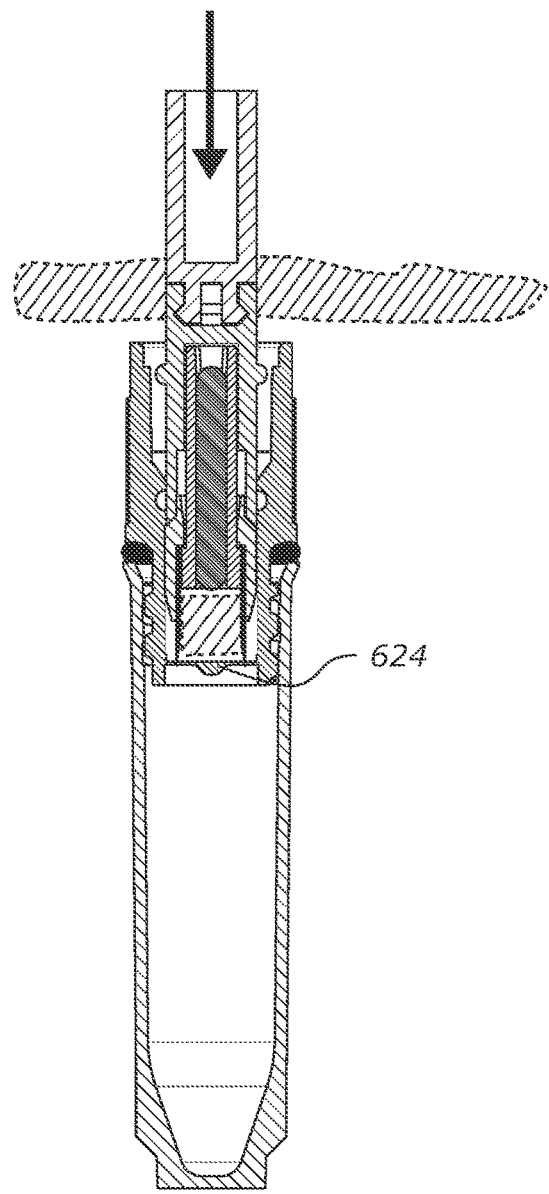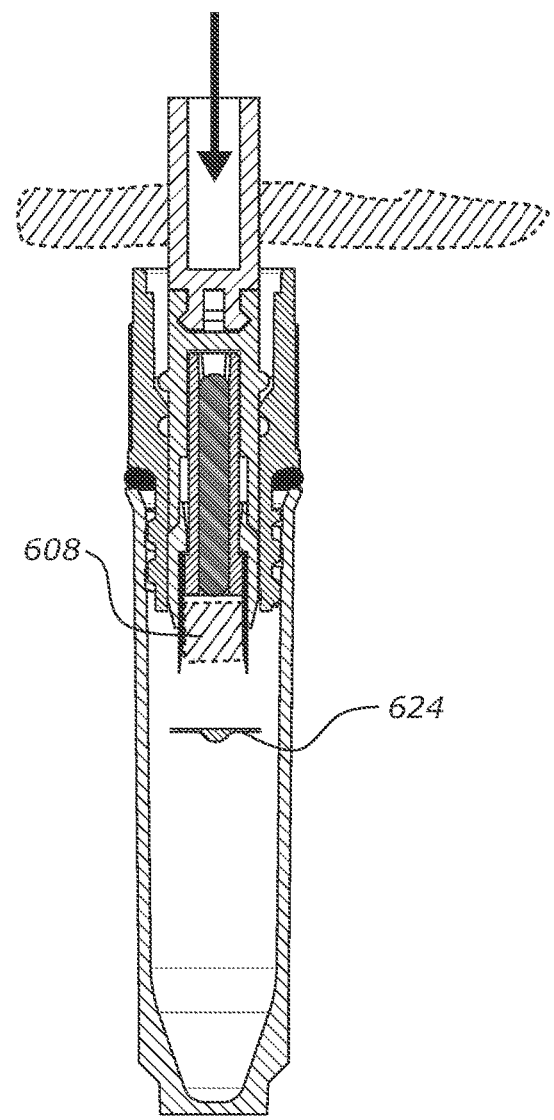
*FIGURE 27* *FIGURE 28*

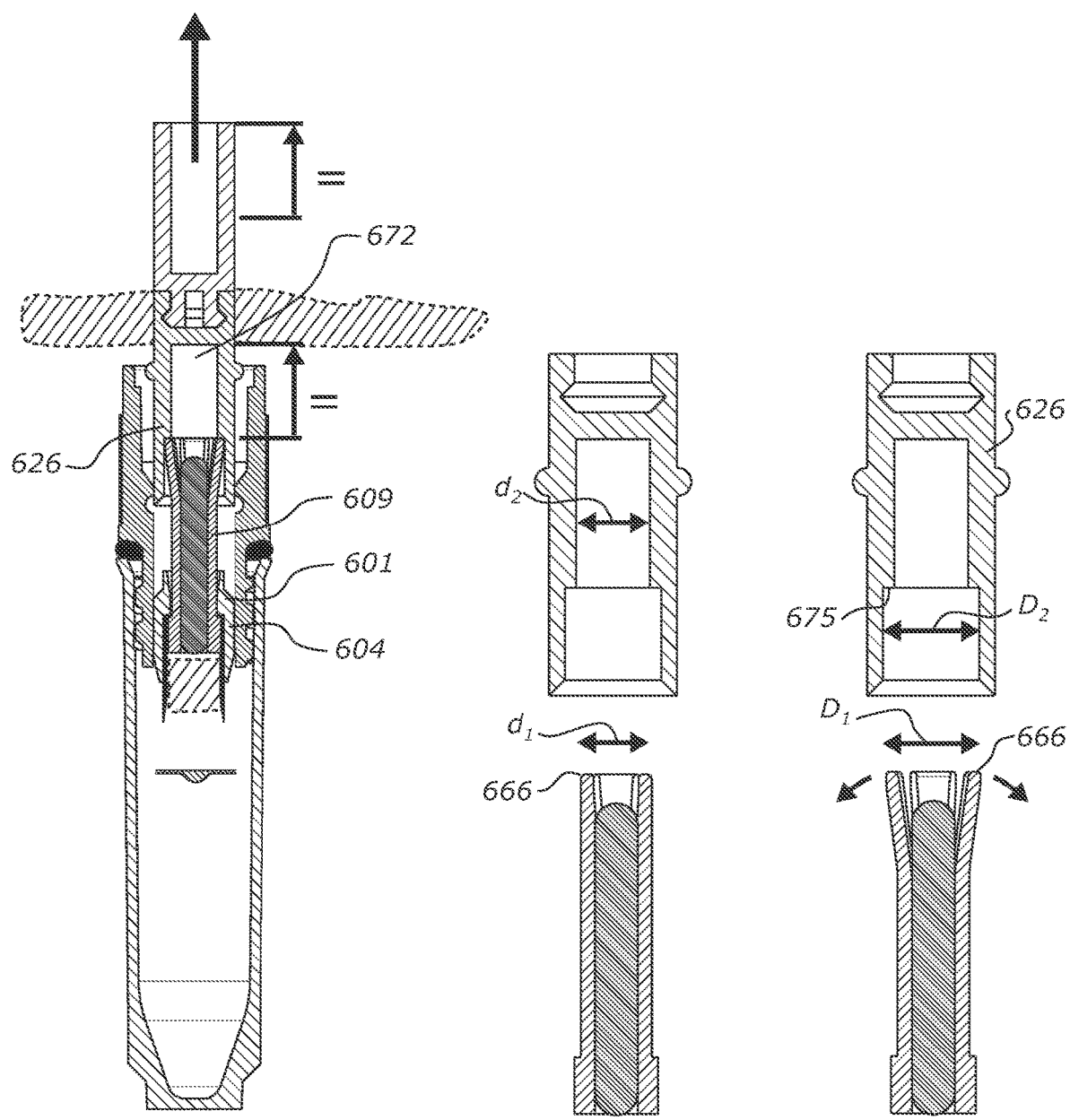
*FIGURE 29*   *FIGURE 30*   *FIGURE 31a*

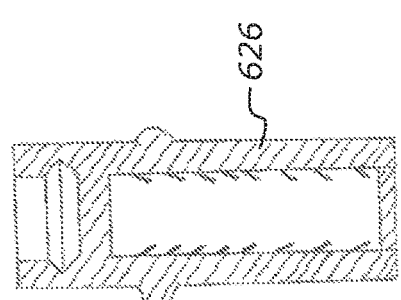
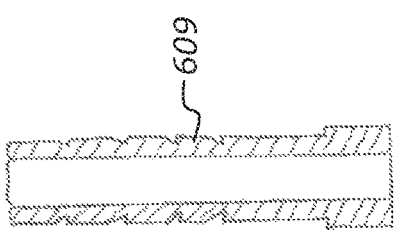
FIGURE 31b
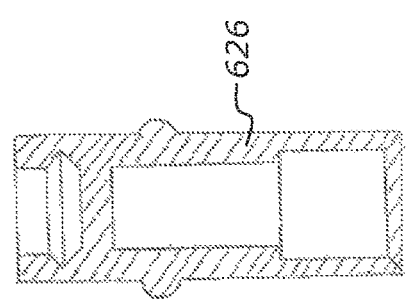
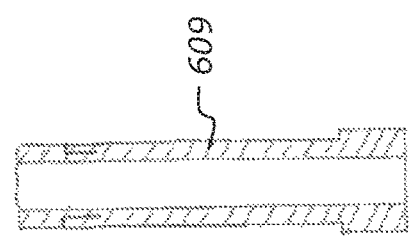
FIGURE 31c
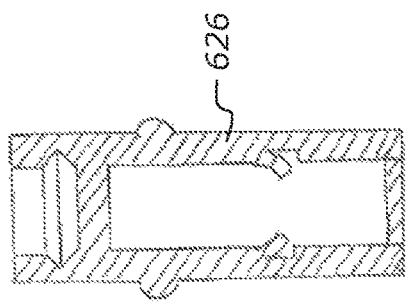
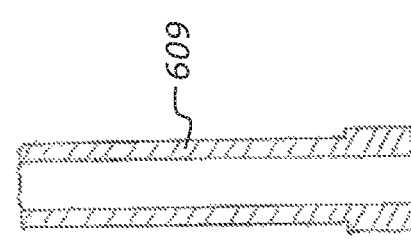
FIGURE 31d
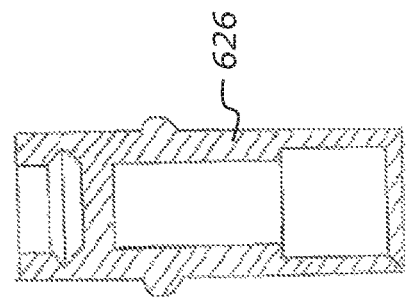
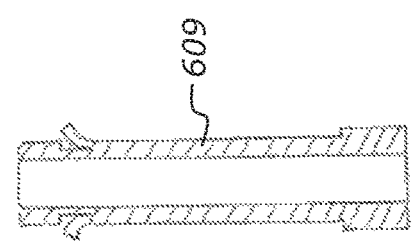
FIGURE 31e
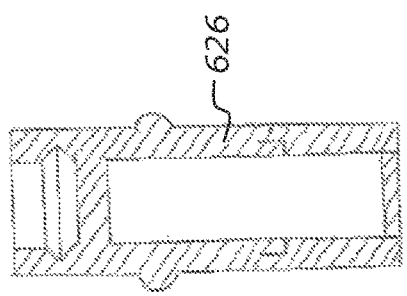
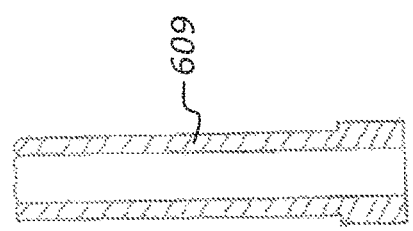
FIGURE 31f

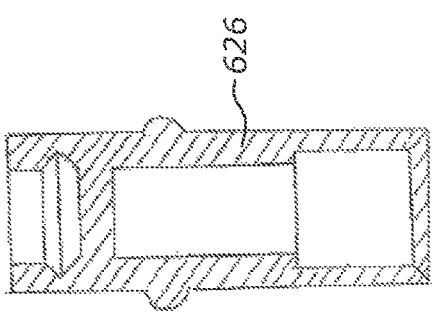
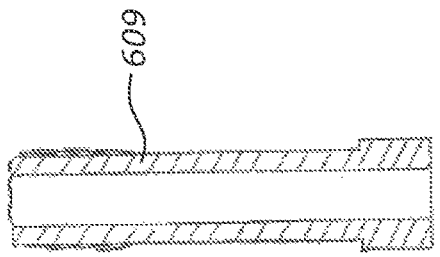
*FIGURE 31g*
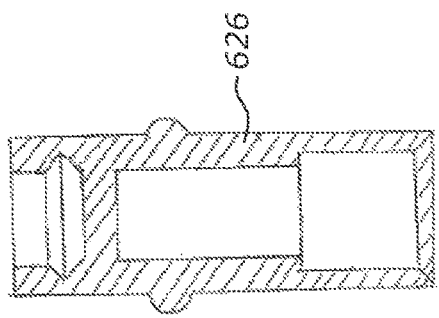
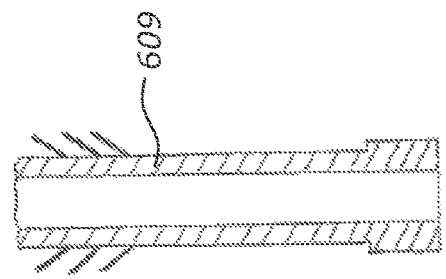
*FIGURE 31h*
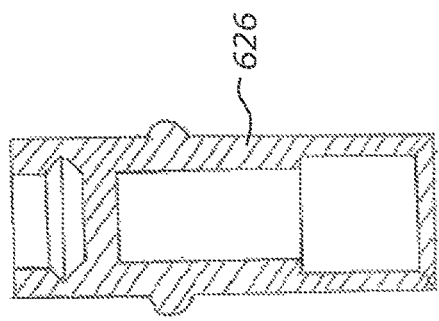
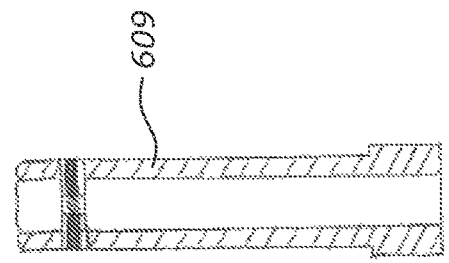
*FIGURE 31i*
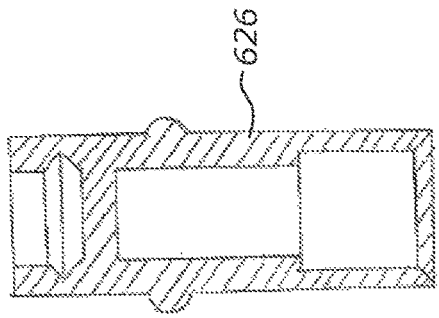
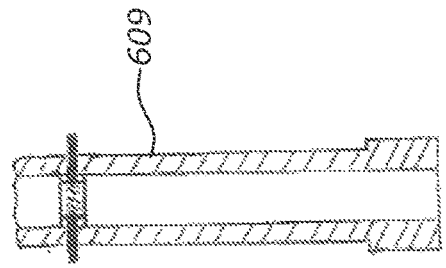
*FIGURE 31j*

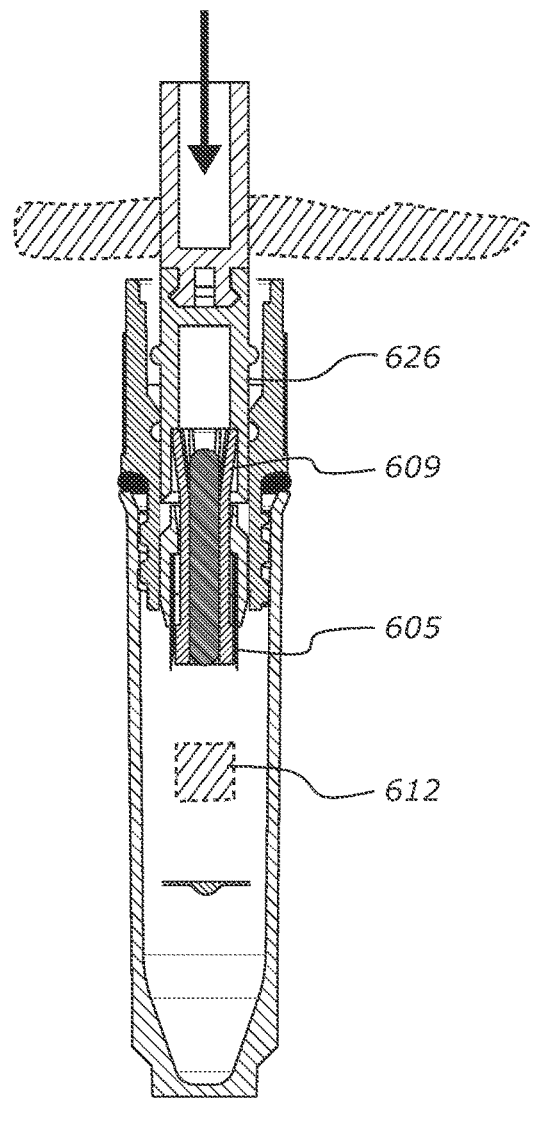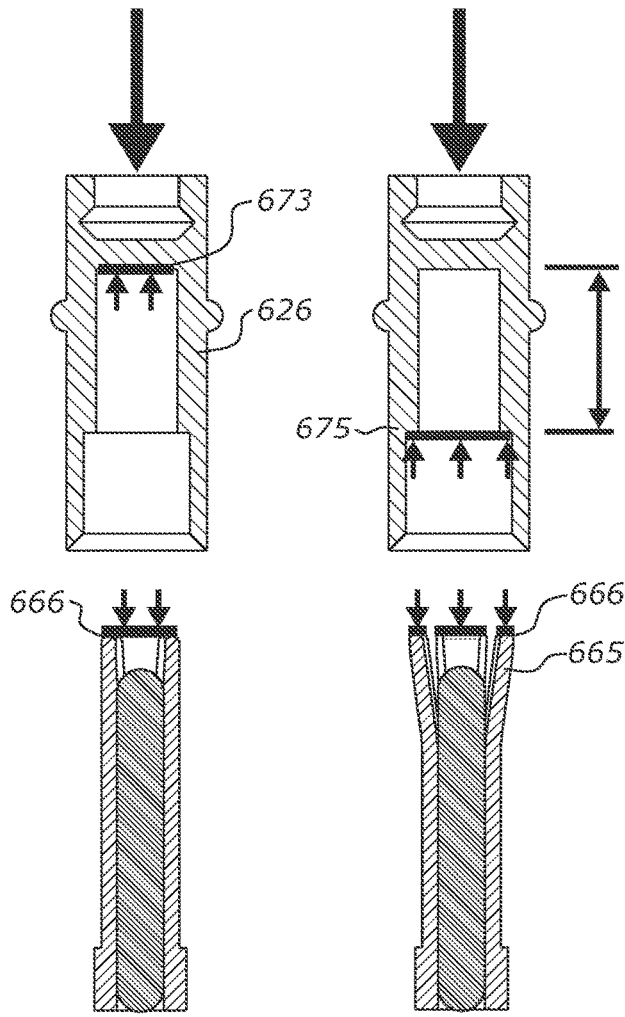
FIGURE 32    FIGURE 33    FIGURE 34

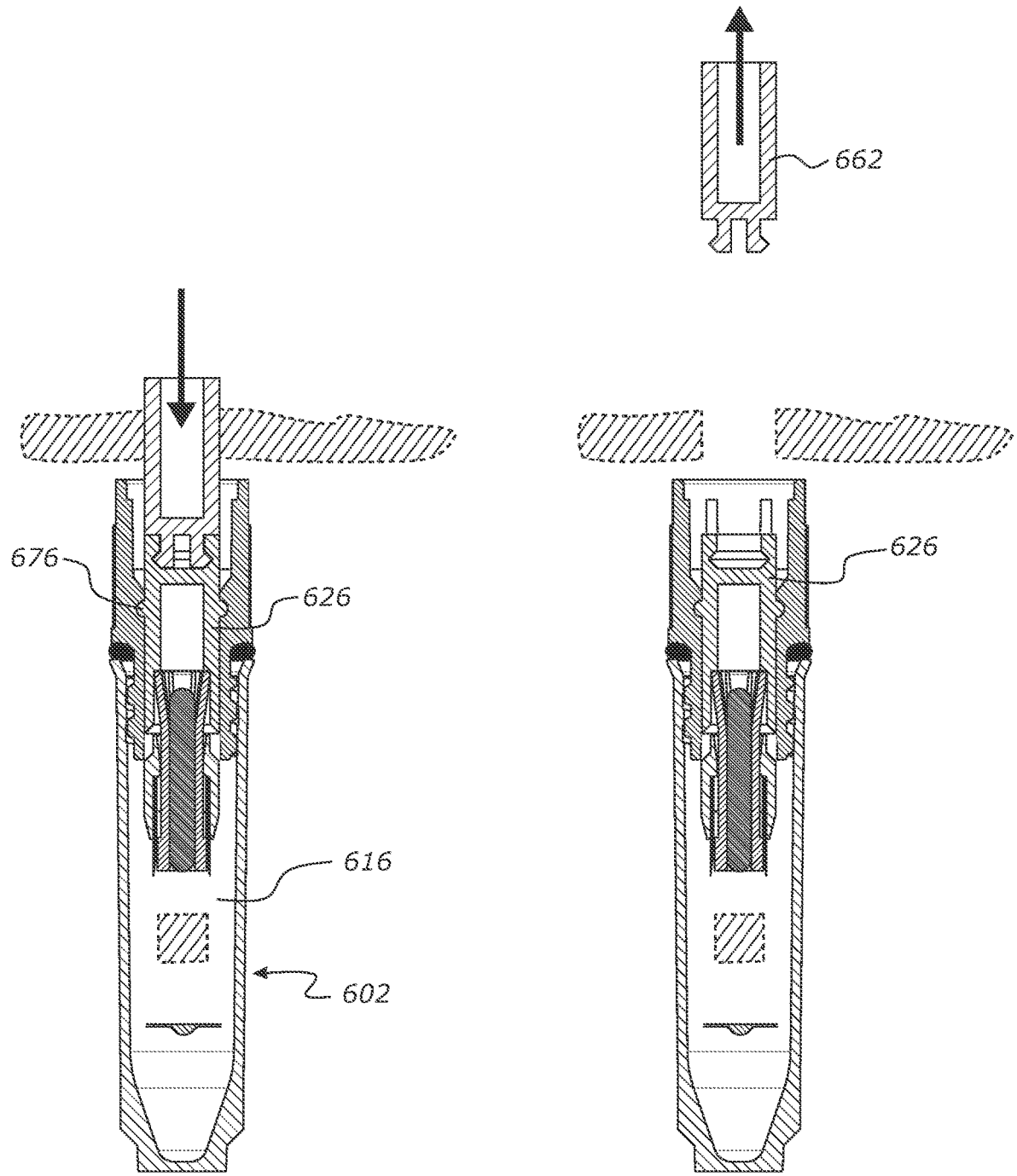
*FIGURE 35*   *FIGURE 36*

QUICK RELEASE DRIVING TOOL

CROSS-REFERENCE TO RELATED APPLICATIONS

This application is a national stage filing under 35 U.S.C. § 371 of International Application No. PCT/IB2017/051115, filed Feb. 27, 2017, which claims priority to U.S. Provisional Application No. 62/305,498, filed Mar. 8, 2016, and U.S. Provisional Application No. 62/316,499, filed Mar. 31, 2016, and further claims priority to New Zealand Application No. 725837, filed Nov. 2, 2016, the entire contents each of which are incorporated herein by reference.

FIELD OF THE INVENTION

The present invention relates to quick release driving tool and in particular but not solely to such a tool to collect biological samples.

BACKGROUND

To facilitate tissue sampling of livestock other animals and plants (such as for subsequent DNA testing), it may be necessary to obtain tissue samples from live animals/plants. Typically a hand-held device is used for obtaining tissue samples from live animals/plants in the field. Such a hand-held device can be used to pierce the skin of the animal or plant to withdraw or collect a sample from the animal or plant.

Piercing of the tissue can cause a degree of pain and fright to the animal. If the animal reacts, for an example by pulling away, before the sampling or tagging operation is complete, then this can cause hurt and/or damage to the animal, the device, or the operator of the device, and may compromise the success of the operation.

In some applications, having obtained a sample, it is desirable to store this sample in a container. Sometimes the container may be carried by the hand-held sampling device used to obtain samples from animals/plants in the field. An example is shown in WO/2014/196877. Movement of an animal or plant during the sampling operation can lead to dislodgement of the sample from a container and/or dislodgement of the container from the handheld device. Therefore it is desirable to containerise the sample and seal the container as soon as possible after the sample has been obtained in order to reduce the risk of losing the sample. This also decreases the risk of foreign matter getting into the sample container to contaminate the sample.

Manual capping of the sample containers can be time-consuming, and may lead to errors, for example if a sample container cap designated to seal a particular container is deliberately or inadvertently swapped to seal a different container. However if containerising and capping of samples is not done manually, but rather is performed automatically by the sampling device, then there can be issues with the cross contamination of sample materials as a result of processing multiple samples with the same device.

It is therefore an object of the present invention to provide a quick release driving tool which overcomes or at least partially ameliorates some of the above mentioned disadvantages, or which at least provides the public with a useful choice.

Where used in this specification tissue means any part of a living thing, particularly any part made up of similar cells, or any part or parts that perform a similar function. Tissue preferably refers to any form of biological sample, from plants and animals particularly, including pigs, goats, cattle, sheep, poultry, and fish. Biological samples may include for example, animal tissue such as flesh, blood, hair, fur, saliva, sweat, urine, etc, or plant tissue such as leaves, bark, roots or wood, or any other part of a plant or animal but particularly those that are made up of similar cells, or which perform a similar function.

The present invention may be used at least for either or both of production animals and companion animals. It is anticipated that production animals may include but not be limited to bovine, pigs, deer and sheep. Further it is anticipated that companion animals may include but not be limited to horses, cats and dogs.

In this specification, where reference has been made to external sources of information, including patent specifications and other documents, this is generally for the purpose of providing a context for discussing the features of the present invention. Unless stated otherwise, reference to such sources of information is not to be construed, in any jurisdiction, as an admission that such sources of information are prior art or form part of the common general knowledge in the art.

SUMMARY OF INVENTION

In a first aspect the present invention may be said to be a quick release apparatus configurable to drive a driven member comprising:

a) a primary driver which provides or carries a driven member, and that is able to drive the driven member in a first direction to an operative position, and b) an actuable secondary driver, said primary and secondary drivers configurable between a first mode, wherein the secondary driver is able to drive the primary driver in the first direction, and in a second mode which allows the primary driver to be moved away from the operative position independent of the position of the secondary driver under the influence of a bias.

In a second aspect the present invention may be said to be an apparatus configurable to drive driven member comprising a body carrying:

a) a primary driver that provides or carries a driven member, and that is able to drive the driven member in a first direction relative the body to an operative position, and b) an actuable secondary driver, wherein the secondary and primary drivers are able to move relative to each other, and in one relative position be caused to couple together and become moveable together, and when in one position relative the body become decoupled to, under the influence of a bias, cause the primary driver to retreat from the operative position and/or direction opposite said first direction.

Preferably the secondary driver is, after retreat of the primary driver relative the operative position, again able to be driven in the first direction and drive the primary driver in the first direction relative the body to complete a driving stroke of the primary driver.

Preferably the primary and secondary drivers are biased to move in a direction opposite the first direction (herein after the "second direction").

Preferably the primary and secondary drivers are caused to move under a bias in the second direction after the completion of the driving stroke.

Preferably the bias is created between the body and one or both of the primary driver and secondary driver and an actuator that causes the secondary driver to be actuated Preferably the actuator is a lever.

Preferably the primary driver is able to be driven over a full driving stroke to push the driven member to or through the item from which a sample is to be taken, wherein the decoupling relative position is reached prior to completing the full driving stroke.

Preferably the retreat from the operative position is not necessarily a return to the beginning of the driving stroke. It is preferably movement in the second direction.

Preferably the driven member is a tissue piercing punch.

Preferably the operative position is an operative tissue piercing position. Preferably the apparatus is a hand-held apparatus.

Preferably the primary driver and secondary driver are adapted and configured to engage each other upon movement of the secondary driver in the first direction and after decoupling.

Preferably the apparatus comprises a trip to trip the drivers from the configuration of the first mode to the configuration of the second mode as the primary driver is driven in the first direction and reaches a trip position.

Preferably the engagement occurs by virtue of two surface contact.

Preferably the engagement occurs by selective engagement of a dog after decoupling.

Preferably the primary and secondary drivers are able to move relative to each other by telescoping one inside the other.

Preferably one or other of the primary driver and the secondary driver has an outwardly projecting shoulder, wherein engagement with each other upon movement of the secondary driver in the first direction and after decoupling occurs by virtue of interference between the shoulder of one driver and a surface of the other driver.

Preferably each of the primary driver and the secondary driver has an outwardly projecting shoulder, wherein engagement with each other upon movement of the secondary driver in the first direction and after decoupling occurs by virtue of interference between the shoulders.

In a further aspect the present invention may be said to be an apparatus configurable to drive a tissue piercing punch comprising a body carrying:

a) a primary driver to engage with the punch (whether directly or indirectly), and b) an actuable secondary driver wherein the secondary driver is able to be actuated to move relative the body from a retreated position to an extended position and the primary driver is able to be driven by said secondary driver relative said body by being releasably coupled to said secondary driver when moving between said retreated position and said extended position to the extended position, save for when the primary driver is momentarily decoupled from said secondary driver, when said secondary driver is at a point between said retreated and extended positions, and under a bias is moved away from the extended position until a second coupling is established between the primary and secondary drivers as the secondary driver moves towards its extended position.

Preferably the punch is part of a sample collector assembly comprising at least a punch, a plunger, and a sample collector driver, and wherein the primary driver engages with the sample collector driver (whether directly or indirectly). Preferably movement of the secondary driver from its retreated position to its extended position causes the primary driver to be driven over a complete driving stroke wherein the primary driver moves from a retreated position relative the body to an extended position relative the body.

Preferably both of the primary and secondary drivers are biased to move in a direction away from the extended position of the secondary driver and back toward the retreated position.

Preferably the primary and secondary drivers are caused to move under a bias, in a direction away from the extended position of the secondary driver and back toward the retreated position, after the completion of the driving stroke.

Preferably the bias is created between the body and one or both of the primary driver and secondary driver and an actuator that causes the secondary driver to be actuated (eg the lever as herein described).

Preferably the primary driver is able to be driven over a full driving stroke to push the punch through the item from which the tissue sample is to be taken, wherein the momentary decoupling of the primary and secondary drivers occurs prior to completing the full driving stroke.

Preferably the movement of the primary driver away from the extended position is not necessarily a return to the beginning of the driving stroke. It is preferably movement towards the retracted position.

Preferably the primary driver and secondary driver are adapted and configured to engage each other in order to establish the second coupling.

Preferably the engagement occurs by virtue of two surface contact.

Preferably the engagement occurs by selective engagement of a dog (e.g. a detent).

Preferably the primary and secondary drivers are able to move relative to each other by telescoping one inside the other.

Preferably one or other of the primary driver and the secondary driver has an outwardly projecting shoulder, wherein the second coupling is established by virtue of interference between the shoulder of one driver and a surface of the other driver.

Preferably each of the primary driver and the secondary driver has an outwardly projecting shoulder, wherein the second coupling is established by virtue of interference between the shoulders.

In yet a further aspect the present invention may be said to be an apparatus to drive a sampling assembly relative to and to collect and dispense a biological sample from an item and into a storage container, said sampling assembly comprising:

a) a sample collector comprising:

a punch presenting at one end a cutter to cut and hold a sample from the item as it passes there through or over, a plunger slideably supported by said punch to be able to move between a retracted position and an advanced position relative said punch, movement from the retracted position to the advanced position causing, in use, the cutter held sample to be displaced from the cutter, b) a tool driver comprising:

a body interfaced with said sample collector in a telescopic manner wherein in telescopically compact position the tool driver can drive the sample collector through the item whilst keeping the plunger in the retracted position so that a sample can be cut and held by the cutter and in a telescopically expanded position the tool driver is able to be driven in the same direction as when driving the collector through the item and cause the plunger to move from its retracted position to its advanced position, the apparatus comprising a body with a storage container holding region at where said storage container can be held and a sampling assembly holding region at where said sampling assembly can be held in a spaced apart manner to define a gap for part of an item to be sampled to placed, the body carrying:

a) a primary driver to engage with the tool driver (whether directly or indirectly), and b) an actuable secondary driver wherein the secondary driver is able to be actuated to move relative the body from a retreated position to an extended position and the primary driver is able to be driven by said secondary actuator relative said body by being releasably coupled to said secondary driver when moving between said retreated position and said extended position to the extended position, save for when the primary driver is momentarily decoupled from said secondary driver, when said secondary driver is at a point between said retreated and extended positions, and under a bias is moved away from the extended position until a second coupling is established between the primary and secondary drivers as the secondary driver moves towards its extended position, the movement away from the extended position of the primary drive causing the sample collector and tool driver to move to the telescopically expanded position so that a when the second coupling is established a driving of the primary driver by the secondary driver will cause the plunger to move to its advanced position.

Preferably the item is pierced by the sample collector after the movement away from the extended position.

Preferably the movement away from the extended position occurs before the primary driver has reached its limit in the extended direction.

Preferably the movement away from the extended position occurs before the primary driver has reached its limit in the extended direction and when said punch is received by said storage container and held by said storage container to resist it moving with the tool driver as it moves away from the extended position.

Preferably the primary driver engages with the tool driver in a manner to be able to move the tool driver in the driving and retracting directions.

Preferably both of the primary and secondary drivers are biased to move in a direction away from the extended position of the secondary driver and back toward the retreated position.

Preferably the primary and secondary drivers are caused to move under a bias, in a direction away from the extended position of the secondary driver and back toward the retreated position, after the primary driver has reached its limit in the extended direction.

Preferably the bias is created between the body and one or both of the primary driver and secondary driver and an actuator that causes the secondary driver to be actuated.

Preferably the movement of the primary driver away from the extended position is not necessarily a return to its limit in the retracted direction. It is preferably movement towards the retracted position.

Preferably the primary driver and secondary driver are adapted and configured to engage each other in order to establish the second coupling.

Preferably the engagement occurs by virtue of two surface contact.

Preferably the engagement occurs by selective engagement of a dog (e.g. a detent).

Preferably the primary and secondary drivers are able to move relative to each other by telescoping one inside the other.

Preferably one or other of the primary driver and the secondary driver has an outwardly projecting shoulder, wherein the second coupling is established by virtue of interference between the shoulder of one driver and a surface of the other driver.

Preferably each of the primary driver and the secondary driver has an outwardly projecting shoulder, wherein the second coupling is established by virtue of interference between the shoulders.

In yet a further aspect the present invention may be said to be an apparatus configurable to drive a tissue piercing punch comprising a body carrying:

a) a primary driver to engage (whether directly or indirectly) with the punch and b) an actuable secondary driver wherein the secondary driver is able to be actuated to move relative the body from a retreated position to an extended position wherein when moving from said retreated position to said extended position:

i. at or between said retreated position and said extended position the primary driver is coupled to said secondary driver to move therewith for an initial delivery stroke ii. between said retreated position and said extended position after said initial delivery stroke the primary driver is decoupled from said secondary driver to, under the influence of a bias move in the direction of the retreated position, and iii. after decoupling, the primary driver is coupled to said secondary driver to move therewith for the final delivery stroke and the primary driver is able to be driven by said secondary driver relative said body by being releasably coupled to said secondary driver when moving between said retreated position and said extended position to the extended position, save for when the primary driver is momentarily decoupled from said secondary driver, when said secondary driver is at a point between said retreated and extended positions, and under a bias is moved away from the extended position until a second coupling is established between the primary and secondary drivers as the secondary driver moves towards its extended position.

In another aspect the present invention may be said to broadly consist in an apparatus configurable to drive a tissue piercing punch comprising a body carrying:

a) a primary driver which provides or carries a tissue piercing punch, said primary driver able to move relative to the body from a retracted position to an extended position to effect a full driving stroke of the punch, during which driving stroke the punch is driven in a first direction through the item from which the tissue sample is to be taken, and b) an actuable secondary driver wherein the secondary and primary drivers are able to move relative to each other, and in a first position relative the body be caused to couple together and become moveable together, and when in a second position relative the body become decoupled to, under the influence of a bias, cause the primary driver to retreat away from its extended position, and wherein said primary driver further comprises:

c) a tertiary driver which provides or carries the tissue piercing punch, and d) a quaternary driver, wherein the tertiary and quaternary drivers are able to move relative to each other, and in a first position relative the secondary driver be caused to couple together and become moveable together, and when in a second position relative the secondary driver become decoupled to, under the influence of a bias, cause the tertiary driver to retreat in a direction opposite the first direction.

Preferably the primary and secondary drivers are able to move relative to each other by telescoping one inside the other.

Preferably the tertiary and quaternary drivers are able to slide relative to the body and/or each other.

Preferably the tertiary and quaternary drivers are able to move relative to each other by telescoping one inside the other.

Preferably the coupling between the tertiary and quaternary drivers is as herein described with respect to the coupling between the primary and secondary drivers.

The sampler/apparatus herein described may be used with a sample collector to be driven by a driver of said apparatus to remove and hold a sample from the item that it can be driven over/through comprising:

a punch presenting a cutter and presenting a driver engageable region to allow the driver to drive said punch to remove said sample from said item, a plunger slideably supported by said punch to be able to move relative said punch between a retracted position and an advanced position, movement from the retracted position to the advanced position causing, in use, the cutter held sample to be displaced from the cutter, the plunger adapted and configured to ratchet with said driver in moving from a first position relative said driver to a second position relative said driver, such that when in said first position said driver not move the plunger from its retracted position to its advanced position and in said second position said plunger is coupled to said driver to allow the driver to move the plunger to its advanced position.

The sampler/apparatus herein described may be used with a sampling string to collect a biological sample from an item, said string comprising:

a) a sample collector comprising:
 a punch presenting at one end a cutter to cut and hold a sample from the item as it passes there through or over,
 a plunger slideably supported by said punch to be able to move between a retracted position and an advanced position relative said punch,
b) a tool driver that in a first condition is engaged said punch to, in use, be able to drive said punch over or through said item,
wherein movement from the retracted position to the advanced position causing, in use, the cutter held sample to be displaced from the cutter, and actuated by a telescopic displacement of the driver from the punch that ratchets the plunger and driver into an operative driving condition.

The sampler/apparatus herein described may be used with a cartridge comprising a body that include a storage container holding region at where a storage container as herein described is located and a sample collector holding region at where a sample collector as herein described is located, preferably with the tool driver engaged with said sample collector in said condition where said plunger is in its retracted position and unable to be moved by said sample collectors driver to its advanced position, there the body holds the sample collector and storage container in alignment with each other for sample taking and spaced apart with a sufficient gap to allow part of an item to be sampled to locate at said gap.

In another aspect the present invention may be said to broadly consist in an apparatus configurable to drive a driven member comprising:

a) a primary driver which provides or carries a driven member and is able to drive the driven member in a first direction to an operative position, and b) a secondary driver which can be coupled to the primary driver by a coupler in order to allow the primary driver to be directly driven by the secondary driver in said first direction, c) a biasing member which can be loaded by either or both of:
 movement of the coupled primary and secondary drivers in the first direction, and
 relative movement of the primary and secondary drivers when uncoupled, and d) a trip to release the coupling as the primary driver reaches its operative position such that the primary driver is caused to retreat from the operative position under the force of the biasing member.

The following apply to the various aspects of the preceding paragraphs of the Summary of Invention, and to any further aspects set out in subsequent paragraphs:

In some embodiments the apparatus/tool further comprises a punch.

In some embodiments the driven member is removable from the primary driver.

In some embodiments said driven member is a punch configured to obtain a tissue sample upon reaching its operative tissue piercing position.

In some embodiments the punch retreats from the operative tissue piercing position along with the primary driver.

In some embodiments movement to the tissue piercing position and retreat from the tissue piercing position by the primary driver is along the same path of travel of the secondary driver.

In some embodiments said punch is part of or associable with a container for collecting tissue samples.

In some embodiments the apparatus further comprises or carries a container, and wherein the punch, upon reaching its operative tissue piercing position, is caused to associate and remain with the container while the primary driver retreats from the operative tissue piercing position.

In some embodiments said punch seals the container upon or after reaching its operative tissue piercing position.

In some embodiments the punch is driven and/or carried along a linear path.

In some embodiments the punch is driven and/or carried along an arcuate path.

In some embodiments the primary driver is driven and/or carried along a linear path.

In some embodiments the primary driver is driven and/or carried along an arcuate path.

In some embodiments the secondary driver is driven and/or carried along a linear path.

In some embodiments the secondary driver is driven and/or carried along an arcuate path.

In some embodiments coupling of the primary and secondary drivers is by way of a mechanical engagement.

In some embodiments the coupling is, for example a detent, pin, catch or fastener.

In some embodiments movement of the secondary driver relative to the primary driver permits or causes coupling of the primary and secondary drivers.

In some embodiments movement of the secondary driver relative to the primary driver aligns or locates the drivers in a position where they can be coupled, for example by a pinned connection extending through both drivers.

In some embodiments movement of the secondary driver relative to the primary driver in a direction opposite the first direction permits or causes coupling of the primary and secondary drivers.

In some embodiments movement of the secondary driver relative to the primary driver causes the displacement of a coupling member to engage the primary and secondary drivers.

In some embodiments further movement of the coupled primary and secondary drivers, said movement being in the first direction, causes the coupling to be released.

In some embodiments further movement of the coupled primary and secondary drivers in the first direction encounters a trip, and wherein engagement with the trip displaces the coupling member to release the coupling.

In some embodiments the biasing member is carried intermediate of the primary and secondary drivers.

In some embodiments movement of the secondary driver relative the primary driver both:
 a) permits or causes coupling of the primary and secondary drivers, and
 b) causes loading of the biasing member.

In some embodiments movement of the secondary driver relative the primary driver in a direction opposite the first direction both:
 a) permits or causes coupling of the primary and secondary drivers, and
 b) causes loading of the biasing member.

In some embodiments the biasing member is a spring.

In some embodiments the biasing member is a compressible member such as a compressible spring.

In some embodiments the primary and secondary drivers are slidable relative to one another.

In some embodiments the primary and secondary drivers are slidable one within the other.

In some embodiments the primary driver is a push rod, and the secondary driver is a push rod driver.

In some embodiments the apparatus is, or is part of, a hand-held device.

In some embodiments the apparatus further comprises a trigger or lever to drive the secondary driver.

In some embodiments the secondary driver is driven on a rack and pinion.

In another aspect the invention can be said to broadly consist in a device to cause the tissue of an animal to be penetrated by a punch, said device comprising:
 a body,
 a push rod that includes a punch end or that can carry a separate punch from, relative said body, a retracted position to an extended position where the punch at least partially penetrates the animal tissue,
 a push rod driver that is mounted to said body, displaceable relative said body by an actuator mounted to said body at least from a first position to a second position, said push rod slideably mounted to said push rod driver to move relative thereto between a primed position and a retreated position,
 a dog, selectively operable between the push rod and push rod driver, that:
  connects said push rod and said pushrod driver so that movement of said push rod driver towards said second position can impart movement of said push rod towards its extended position,
  is tripped when the push rod reaches its extended position to release the push rod from its primed position and cause the push rod to slide to its retreated position to or towards its retracted position under the influence of a bias.

In some embodiments the bias is provided by a spring that acts between the push rod and one of (a) the body and (b) the push rod driver.

In some embodiments the bias is provided by a spring that acts between the push rod and the push rod driver.

In some embodiments the spring is loaded when the push rod driver is moved from its second position towards its first position.

In some embodiments the spring is unloaded when the dog is tripped.

In some embodiments the spring is a helical spring.

In some embodiments the spring is loaded by virtue of being compressed.

In some embodiments the spring is unloaded by virtue of its expansion.

In some embodiments the dog connects said push rod and said pushrod driver so that the push rod driver can move the push rod, when the push rod is in its primed position.

In some embodiments the dog, when tripped, allows the push rod to slide relative said push rod driver.

In some embodiments the push rod moves to its primed position when the push rod driver moves towards its first position from its first position.

In some embodiments the push rod is restrained by the housing from movement with said push rod driver when the push rod driver is moving to its first position.

In some embodiments when the push rod is restrained by the housing the spring acting between the push rod and the push rod driver is compressed when the push rod driver is moved to its first position.

In some embodiments the actuator is able to also move the push rod driver from its second position to its first position.

Alternatively In some embodiments the push rod driver is caused to be moved from the second position to the first position under the influence of a bias (eg In some embodiments by a spring).

In some embodiments the push rod is displaceable relative said body in a linear manner.

In some embodiments the push rod driver is displaceable relative said body in a linear manner.

In some embodiments the push rod is displaceable relative said body in a linear manner.

In some embodiments the push rod is displaceable relative said push rod driver in a linear manner.

In some embodiments the push rod is displaceable relative said body in an arcuate manner.

In some embodiments the push rod driver is displaceable relative said body in an arcuate manner.

In some embodiments the push rod is displaceable relative said body in an arcuate manner.

In some embodiments the push rod is displaceable relative said push rod driver in an arcuate manner.

In some embodiments the penetrating device is a tissue sample collector.

In some embodiments the penetrating device is provided as part of the end of the pushrod.

In some embodiments the penetrating device is a shaft of an ear tag carried by the push rod.

In some embodiments the punch is a tissue sampling punch.

In some embodiments the punch is able to be releasably mounted at the end of the push rod.

In some embodiments the device is hand operable.

In some embodiments the device is a hand held device.

In some embodiments the body is able to be held in the hand of a user.

In another aspect the present invention can be broadly said to consist in an apparatus able reciprocate a driver or punch (hereafter 'punch') (1) to an advance limit under the indirect action of an actuator and (2) to withdraw the punch from its advance limit initially under the action of a compression bias and then under the indirect action of the or another actuator, the apparatus comprising or including:

the punch, a receiver that partly receives the punch so as to enable relative movement on the axis of reciprocation, a support to guide and limit, or guide, limit and at least partly house, the receiver between limits of its reciprocation on the axis of reciprocation, a compressible member acting to bias the punch from its advance limit relative to the receiver, a detent that operates between the punch and receiver for the simultaneous advancement of the punch and receiver to their respective advance limits, and an actuator or actuators to control the reciprocation of the receiver relative to the support.

In some embodiments the reciprocation is rectilinear.

In some embodiments the punch is captured against release from the receiver in the advance direction.

In some embodiments the support provides a stop to limit the advance of the receiver.

In some embodiments the support provides a cam to release the detent.

In some embodiments the support provides a cam to engage the detent.

In some embodiments the detent is ball detent.

In some embodiments the or at least one actuator acts directly or indirectly on a rack of the receiver.

Preferably the punch is able to be driven through the organism.

Preferably one (or more) of the invention(s) herein described may be used for production animals and for companion animals.

Preferably one (or more) of the invention(s) herein described may only be used for production animals.

Preferably one (or more) of the invention(s) herein described may only be used for companion animals.

Preferably production animals include but are not limited to bovine, pigs, deer and sheep.

Preferably companion animals include but are not limited to horses, cats and dogs.

Other aspects of the invention may become apparent from the following description which is given by way of example only and with reference to the accompanying drawings.

As used herein the term "and/or" means "and" or "or", or both.

As used herein "(s)" following a noun means the plural and/or singular forms of the noun.

The term "comprising" as used in this specification means "consisting at least in part of". When interpreting statements in this specification which include that term, the features, prefaced by that term in each statement, all need to be present but other features can also be present. Related terms such as "comprise" and "comprised" are to be interpreted in the same manner.

The entire disclosures of all applications, patents and publications, cited above and below, if any, are hereby incorporated by reference.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.)

BRIEF DESCRIPTION OF THE DRAWINGS

The invention will now be described by way of example only and with reference to the drawings in which:

FIG. 3: shows a cross sectional view of the mechanism of FIG. 2 through the plane C-C, FIG. 5: shows a cross sectional view of the mechanism of FIG. 4 through the plane C-C.

FIG. 21 shows an exploded view of a storage container axially aligned with a sample collector and tool driver plus an associated push rod, FIG. 22 is an exploded view of the string of components comprising of the sample collector comprising of the punch and plunger and the tool driver and push rod, FIG. 23a is a cross sectional view through the components of FIG. 21 showing the plunger with its umbrella in an expanded, drivable condition, FIG. 23b shows the umbrella of the plunger in a contracted condition, FIG. 25 is a cross sectional view of the components of FIG. 24 with the cutter of the sample collector having punctured the ear of the animal, FIG. 26 is a cross sectional view of the components of FIG. 24 wherein the sample that has been collected from the ear of the animal is driven into the storage container, FIG. 27 shows the components of FIG. 24 and wherein the punch is about to rupture the frangible seal of the cap of the storage container, FIG. 28 is a view of the components of FIG. 24 wherein the frangible seal has been ruptured to allow for the sampler to enter the storage region of the storage container, FIG. 29 shows the step in the process of the components of FIG. 24 wherein the tool driver has retreated back towards its pre-delivery position in order to cause a telescopic movement relative to the plunger and allow for the two components to ratchet to a second condition so that the plunger is then able to be actuated to move to an advanced position by the sample collector, FIG. 30 is a cross sectional view of the tool driver and the plunger, the plunger and its umbrella shown in a contracted condition, FIG. 31a is a view of FIG. 30 but wherein the umbrella of the plunger is shown in unexpanded condition, FIGS. 31b-j show variations of the telescopic ratchet relationship that can be established between the tool driver and the plunger in order to allow for the plunger and the tool driver to move between a retracted and advanced position and where a ratcheting relationship is provided by varying features of the tool driver and the punch, FIG. 32 shows the tool driver and plunger in a telescopically expanded relationship, the plunger still being in a retracted condition relative to the punch but in a position able to be driven by the tool driver to an advanced position, FIG. 33 illustrates the tool driver and plunger indicating that contact may exist between the interior wall of the tool driver and the driving end of the plunger, FIG. 34 shows the tool driver and plunger wherein the plungers umbrella is in an expanded condition able to then be driven by a different surface of the tool driver, FIG. 35 illustrates the tool driver having been advanced, after the momentary retraction, back towards the storage containment region in order to then drive the plunger relative to the punch to cause the sample to drop into the storage containment region and wherein the tool driver has engaged at the passage of the cap of the storage container in order to seal the storage container, FIG. 36 shows the push rod having been retracted from the tool driver and the sampling and storage process being complete.

DETAILED DESCRIPTION

Figure 1:
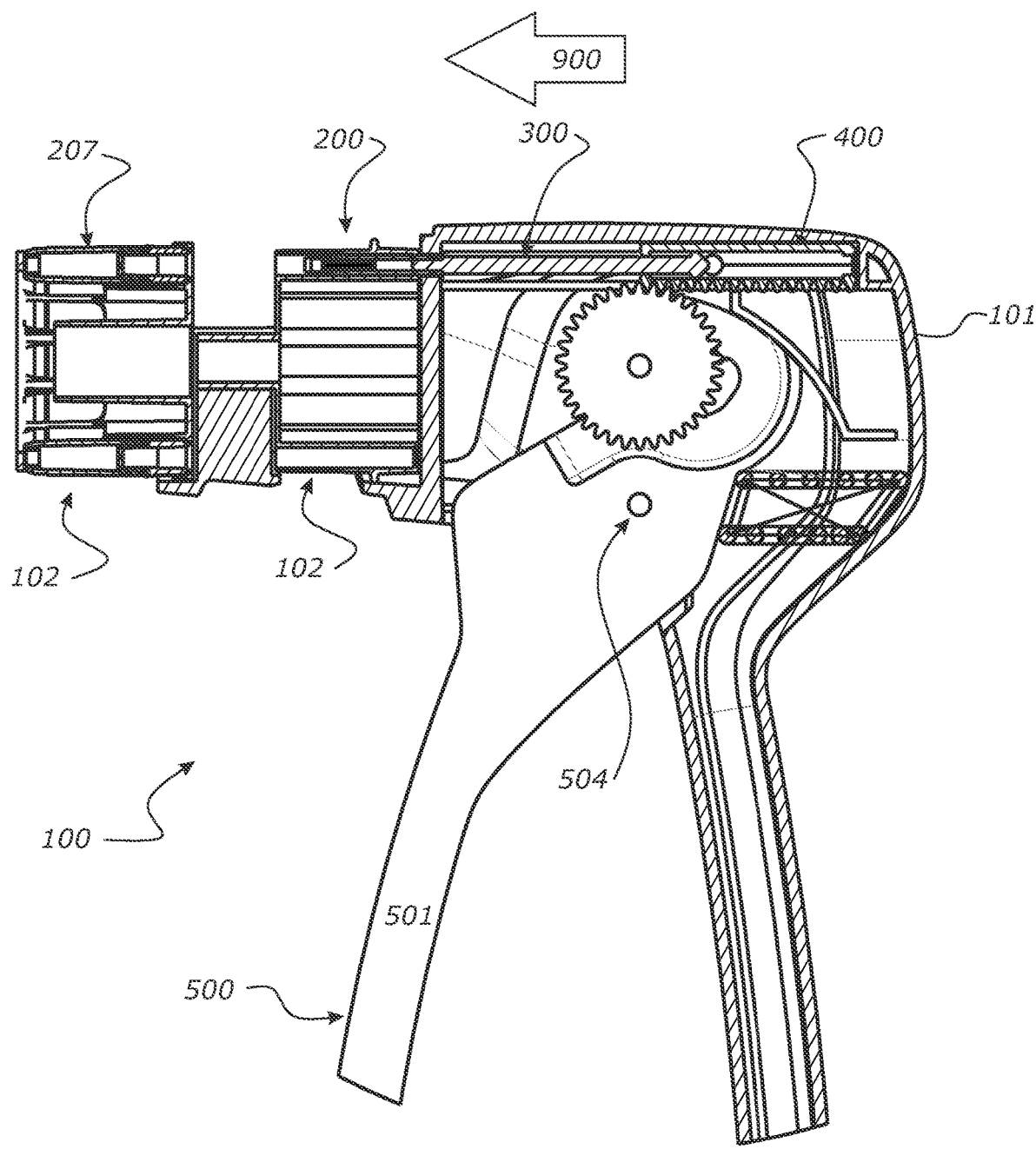
FIG. 1: shows a cross sectional side view of an embodiment of the quick release driving tool, being a tissue sample collector with rotary magazines for storing punches and tissue sample collection containers.
Figure 2:
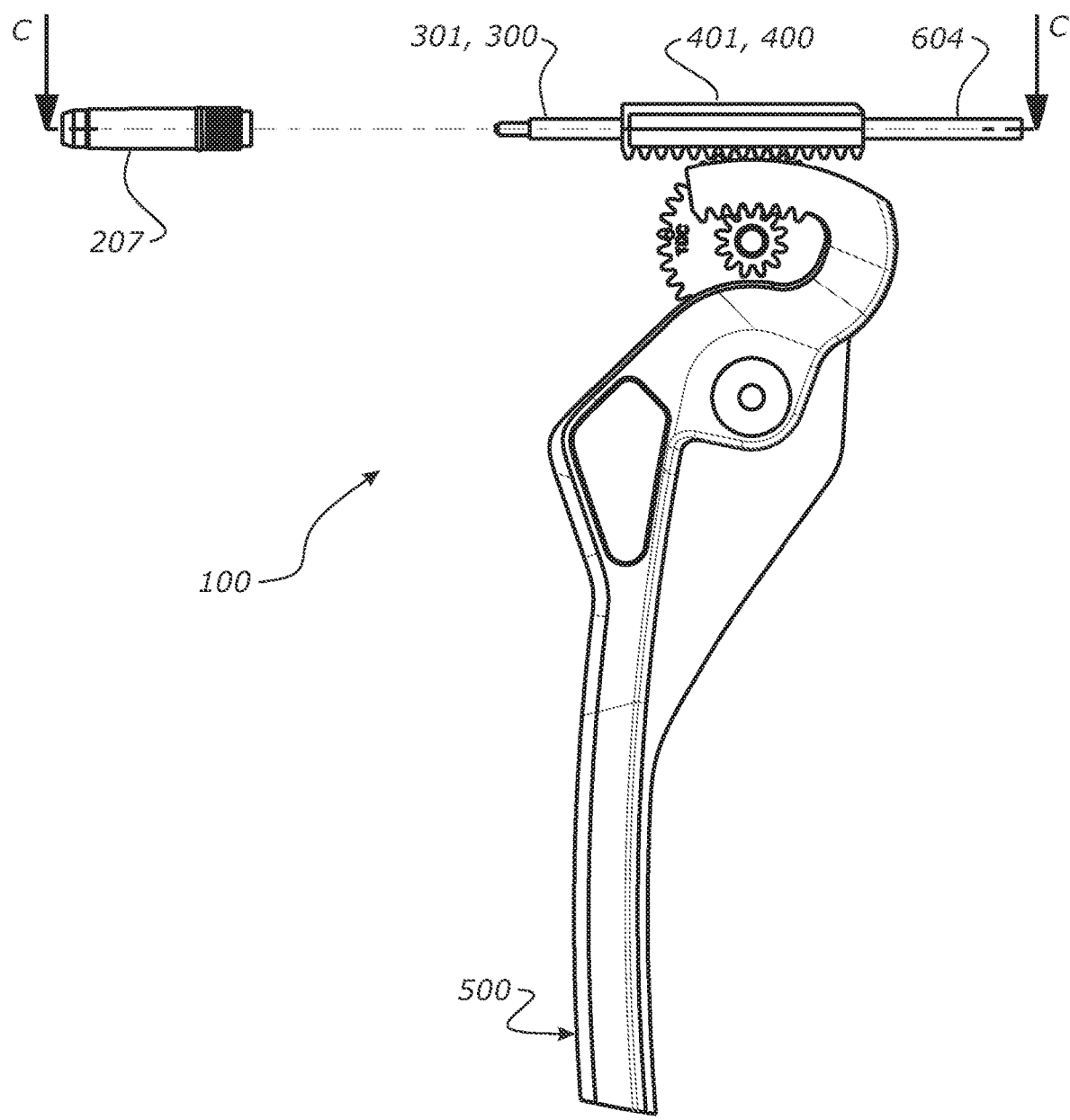
FIG. 2: shows a side view of a part of the mechanism that may be used in the tool.

In one embodiment now described in FIG. 1, there is provided a quick release tool 100. It is preferably configured to drive a punch for piercing an item such as animal tissue in order to collect a tissue sample. It is envisaged that, at least in some embodiments, the quick release tool 100 may be a hand-held device which can be used on live animals or plants in the field. While the invention has been described in respect of its use on animals such as livestock or companion animals, a person skilled in the art will appreciate that it could be used in the same manner on plants.

FIG. 1 shows an embodiment of a quick release tool 100 with rotary magazines 102 for storing sample collection containers 207 and punch attachments 200. FIGS. 2 to 11 show more detail of the a mechanism employed.

The quick release tool 100 has a body 101 which can be held in the hand of an operator. In a preferred embodiment the quick release tool 100 operates as a tissue sampler and is configured to drive a punch 200 to pierce the tissue of an animal. An actuator 500 can be used by the operator to actuate driving of the punch 200.

In some preferred forms the tool 100 comprises a primary driver 300 and a secondary driver 400, supported by and able to move relative to the body 101. The primary and secondary drivers 300,400 are also able to move relative to one another, but can be selectively coupled together to in order to drive the driven member such as the punch 200 when the tool operates as a tissue sampler.

The punch 200 is provided to pierce the tissue of the animal by penetrating some way into or through the tissue. The punch 200 is driven in a first direction (shown by arrow 900) to an operative tissue piercing position, where it engages with the tissue to be pierced. The operative positions of the primary and secondary driver 300,400 respectively can be said to be their corresponding positions (relative the body 101) when the punch 200 is in its operative position.

The tool 100 can be positioned so an ear 203 of the animal lies between the punch 200 and a receiving member such as a container 207. The punch 200 is able to be driven to an operative tissue piercing position, shown in FIG. 13, where the punch 200 has penetrated through the ear 203 of the animal and has been received by the receiving member 207.

At this point, it is desirable to swiftly retract the primary driver 300 to be clear of the ear 203 as the animal reacts to the tissue piercing sensation. To achieve this "quick release" of the primary driver 300, the coupling between the primary driver 300 and the secondary driver 400 may be released as (perhaps shortly before or after) the operative tissue piercing position is reached to allow the primary driver 300 to retreat from its operative position. There is in some embodiments a biasing member 805 to drive the swift retreat of the primary driver 300.

In some embodiments the primary and secondary drivers 300,400 are housed within the body 101, the body 101 serving to guide and limit the movement of the drivers. The drivers are also in some embodiments movable relative to one another. For example they may slide relative to one another, and relative to the body 101. The primary and secondary drivers 300,400 may be moved relative to one another to allow or cause them to become coupled together in a first mode of configuration. In this first mode, using the actuator 500 to drive the secondary driver 400 will cause the primary driver 300 and punch 200 to be driven to the operative position.

There may also be a trip 700 to automatically release the coupling 800 as the operative position of the punch 200 is reached. The trip 700 may be encountered as the coupled drivers move in the first direction 900. The trip 700 causes the primary and secondary drivers 300,400 to assume a second mode of configuration in which the primary driver 300 is able to move independently of the secondary driver 400 and thus retreat from its operative position.

It is also preferable that relative movement of the drivers to effect coupling and/or as they move toward the operative position in their first mode configuration causes loading of the biasing member 805. This enables the loaded biasing member 805 to drive the primary driver 300 back from its operative position once the trip 700 releases the coupling 800.

In some preferred embodiments a single motion of the actuator 500 can effect the driving stroke of the driven member 200 (preferably a punch 200) with the primary and secondary drivers 300,400 configured in their first mode, and no subsequent motion or action is required on the part of the operator in order to release the coupling so that the primary driver 300 can retreat under the force of the biasing member 805.

Components of an exemplary mechanism is shown in FIGS. 2 to 11, where the primary driver 300 is a push rod 301 with a driven member 200 as an attachment, and the secondary driver 400 is a push rod driver 401 actuated on a rack and pinion 502. The push rod 301 is received by and slides axially within the push rod driver 401. The biasing member 805 is, in this example, a spring 806 mounted intermediate of the push rod 301 and the push rod driver 401.

Figure 6:
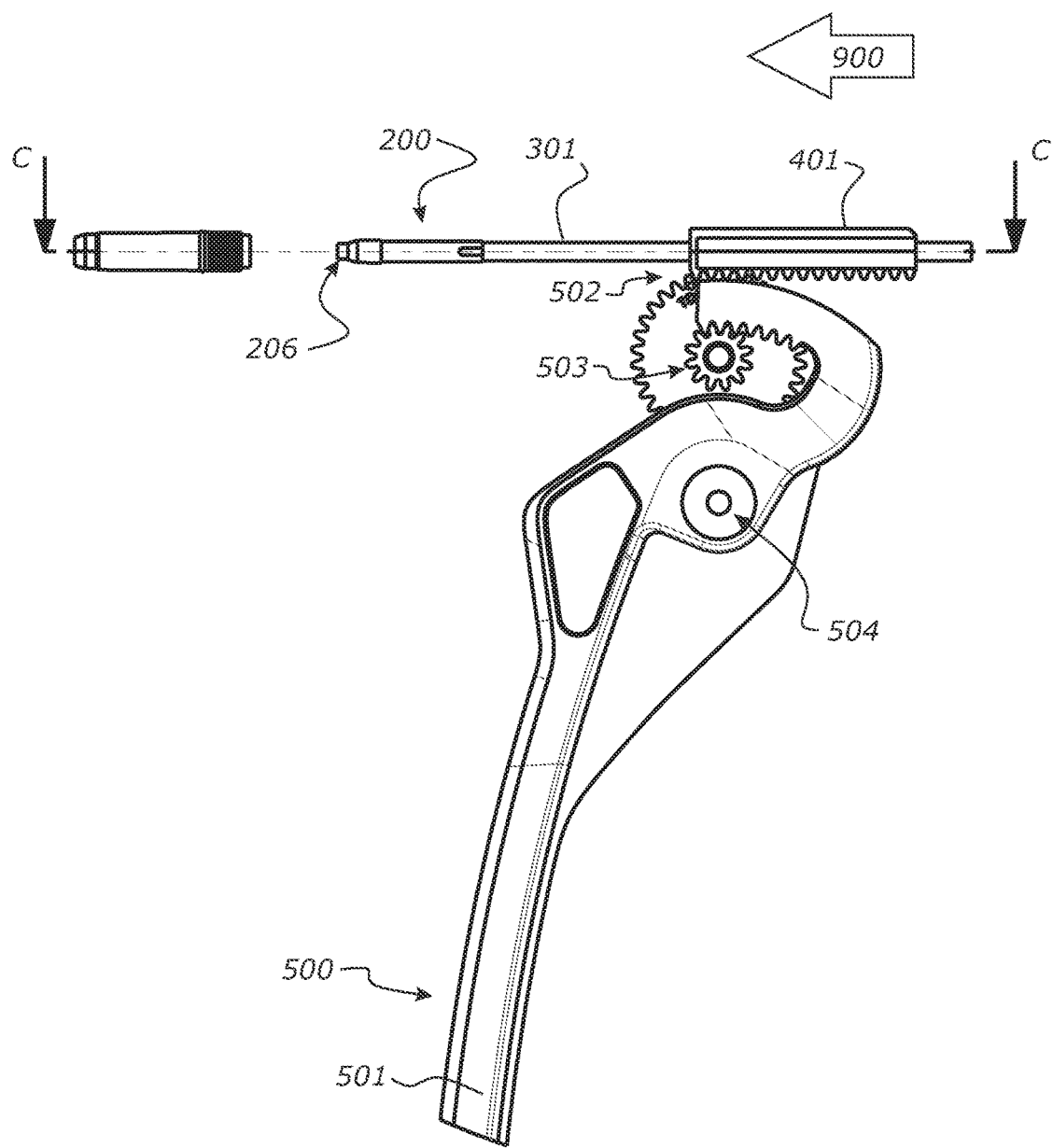
FIG. 6: shows the mechanism of FIG. 4, where an actuator has been engaged to drive the coupled primary and secondary drivers in a first direction toward their operative positions.
Figure 7:
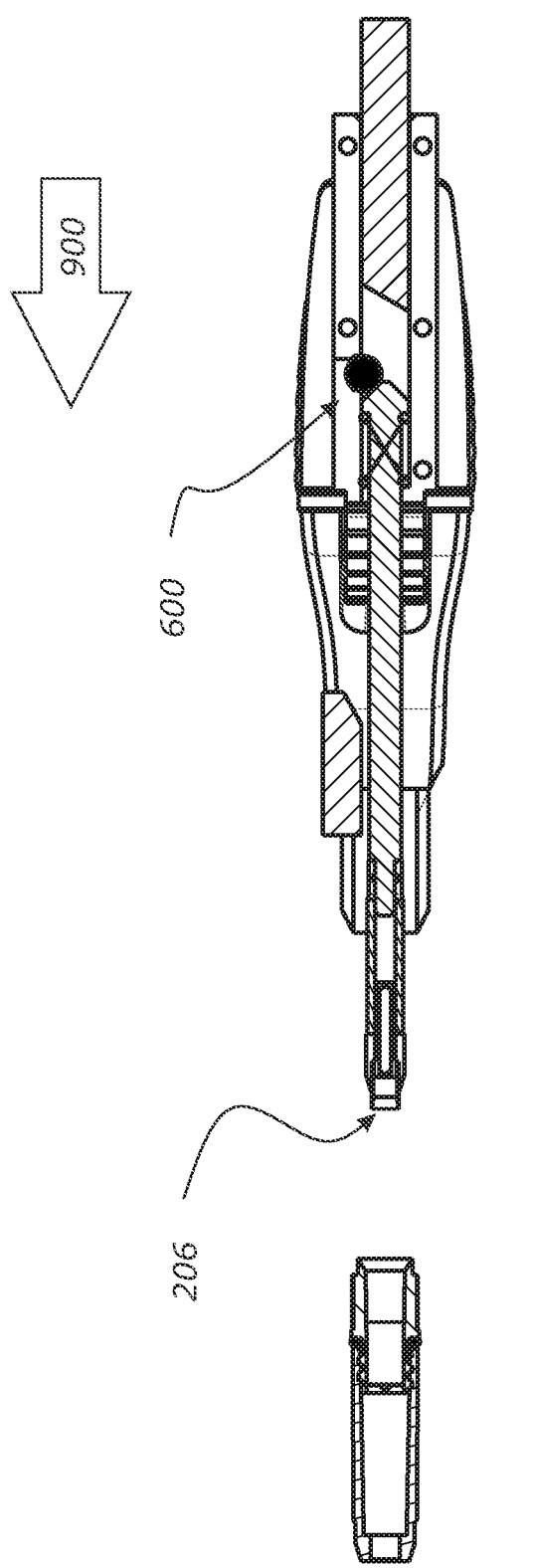
FIG. 7: shows a cross sectional view of the mechanism of FIG. 6 through the plane C-C.
Figure 8:
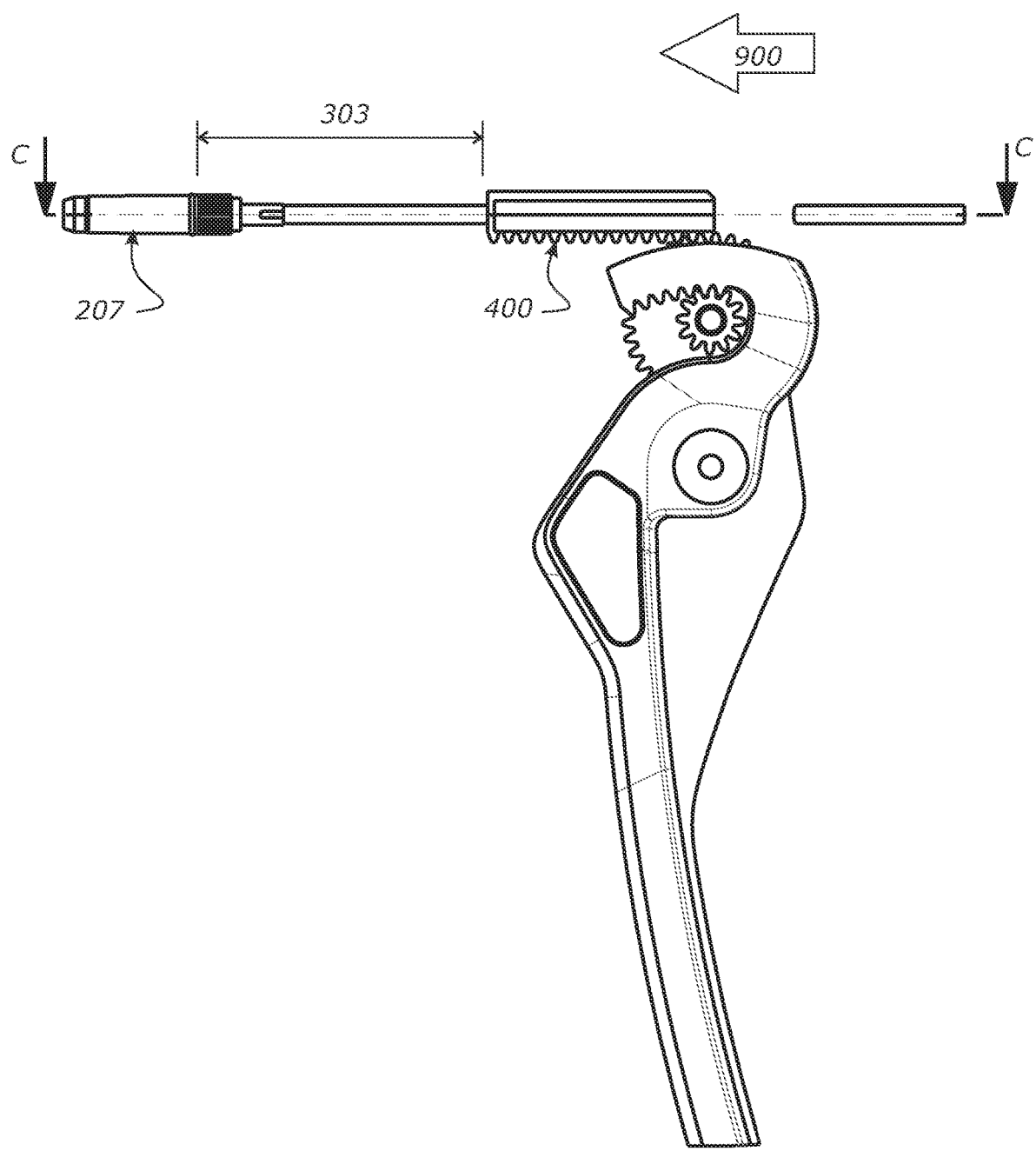
FIG. 8: shows the mechanism of FIG. 6, wherein a punch has been driven to its operative position, and wherein a trip has been encountered to release the coupling between the primary and secondary drivers.
Figure 9:
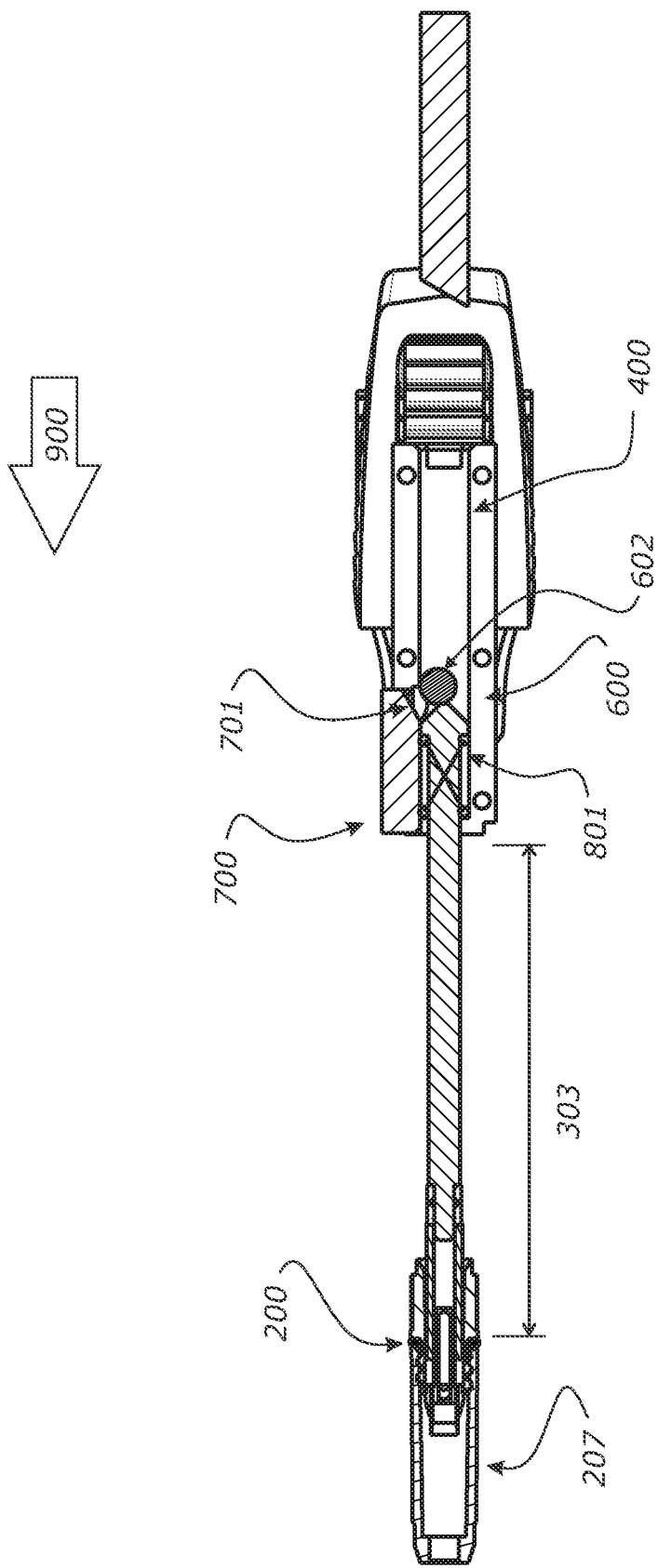
FIG. 9: shows a cross sectional view of the mechanism of FIG. 8 through the plane C-C.

The pushrod is driven between a retracted position (relative to the body 101) which can be seen in FIGS. 2 to 11 and an extended position (relative to the body 101) which can be seen in FIGS. 8 and 9. Similarly, the push rod driver 401 reciprocates between a first position (relative to the body 101) shown in FIGS. 4 and 5 and a second position (relative to the body 101) shown in FIGS. 8 to 11.

Relative movements of the primary and secondary drivers 300,400 in order effect the driving stroke of the driven member 200 and the subsequent swift retreat of the drivers are shown in sequence in the FIGS. 1 to 11. In the following description the direction of the driving stroke, shown by arrow 900 in the Figures, is referred to as the first direction 900. The opposite direction, shown by arrow 901 in the Figures, is referred to as the second direction 901.

Figure 4:
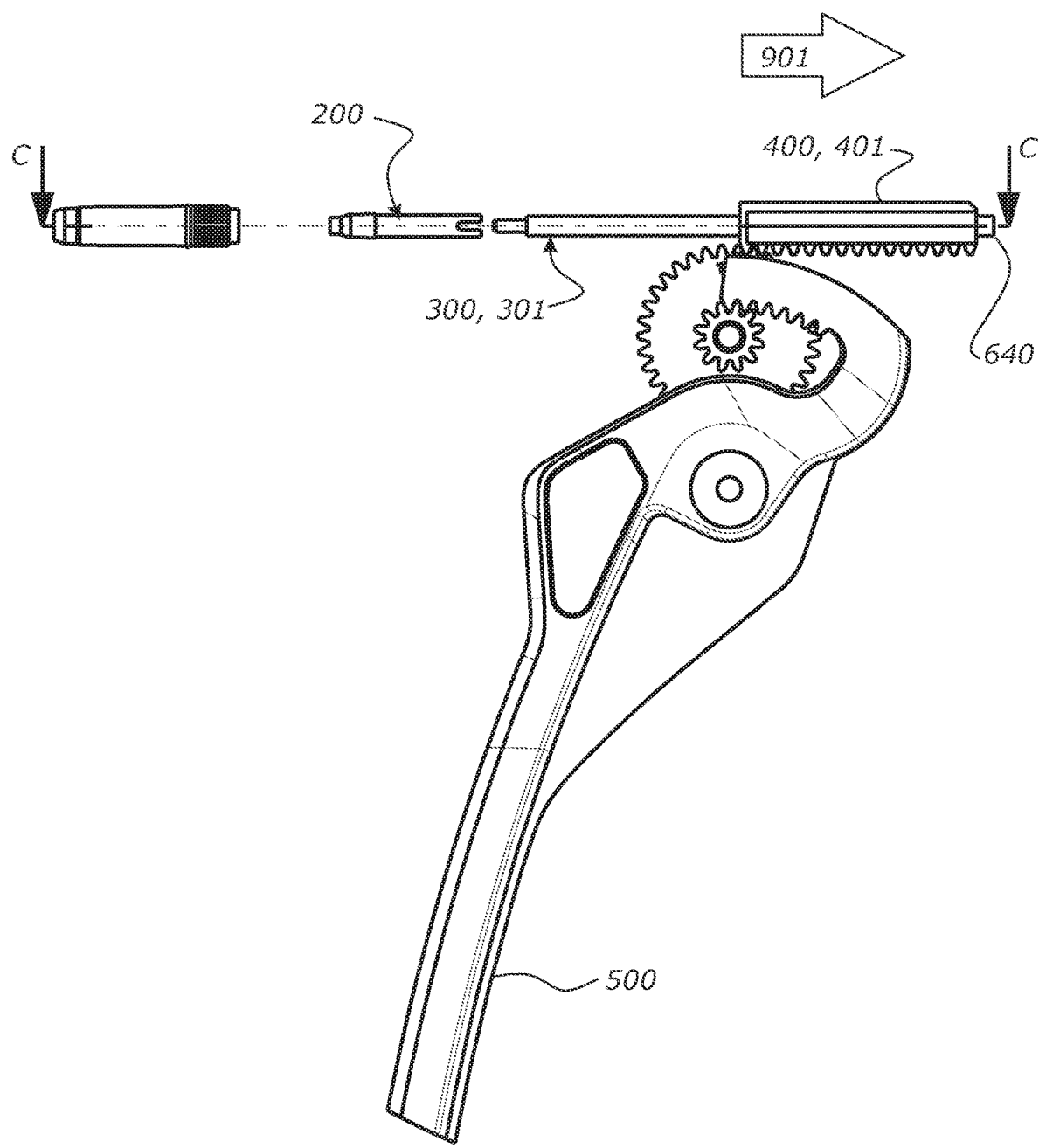
FIG. 4: shows the mechanism of FIG. 2, wherein a secondary driver has been moved in a second direction so as to compress a biasing member and couple with a primary driver.

The sequence begins with the push rod 301 in its retracted position (relative to the body 101) and the push rod driver 401 in its second position (relative to the body 101) as shown in FIGS. 8 and 9. As shown in FIGS. 4 and 5, the push rod driver 401 is then moved in the second direction 901 to its first position. As the push rod driver 401 moves in the second direction 901, the corresponding movement of the push rod 301 in the second direction 901 is limited by a stop 804. Thus there is relative movement of the push rod 301 and driver 401 which compresses the spring 806 between them.

As the push rod driver 401 reaches its first position, the push rod and push rod driver are coupled together by a detent 801, as shown in FIG. 5. The detent engagement relies upon a ball 802 intermediate of the push rod end 301 and the stop 804 being displaced radially outward of the push rod axis, guided on angled surfaces 302 of the push rod end 301 and stop 804. The ball 802 is displaced into a corresponding recess 803 of the push rod driver 401. Thus the push rod 301 is coupled to the pushrod driver 401 with the push rod 301 in a primed position (relative the driver), and the coupling 800 also holding the spring 806 in its compressed condition.

As shown in FIGS. 6 to 8 the actuator 500 is engaged to drive the coupled push rod 301 and push rod driver 401 in the first direction 900, carrying the compressed spring 806 with them.

As the push rod driver 401 advances to its second position (relative the body 101), the coupled drivers encounter the trip 700, which is in this case a camming surface 701. This can be seen in FIG. 9. Movement of the coupled drivers in the first direction 900 relative to the camming surface 701 causes the detent ball 802 to be guided or displaced radially inward to release the coupling 800. In some embodiments the release occurs just as the push rod driver 401 reaches its fully extended position (relative the body 101).

Figure 10:
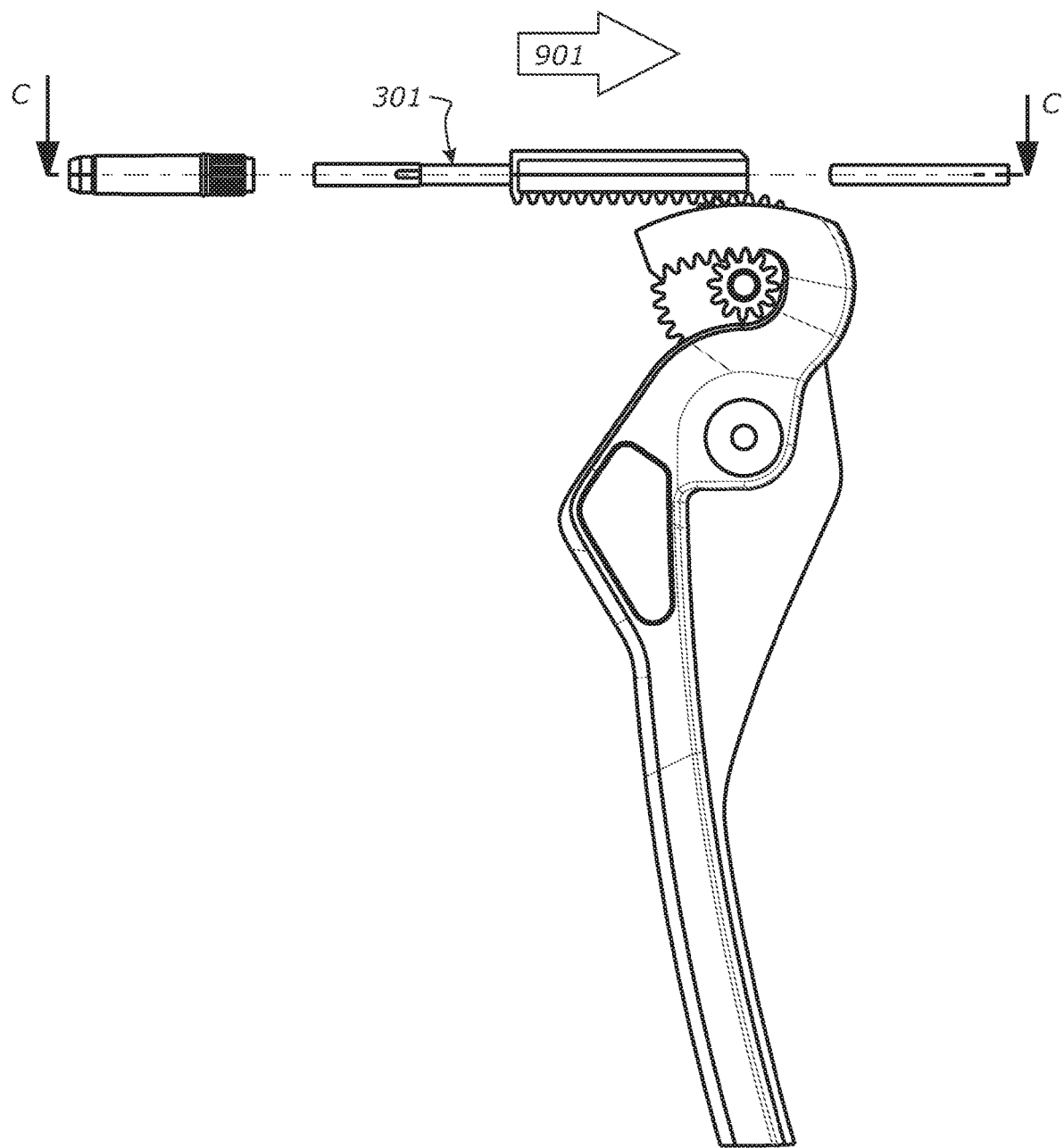
FIG. 10: shows the mechanism of FIG. 14, wherein the primary driver has been driven to retreat from its operative position under the action of a biasing member.
Figure 11:
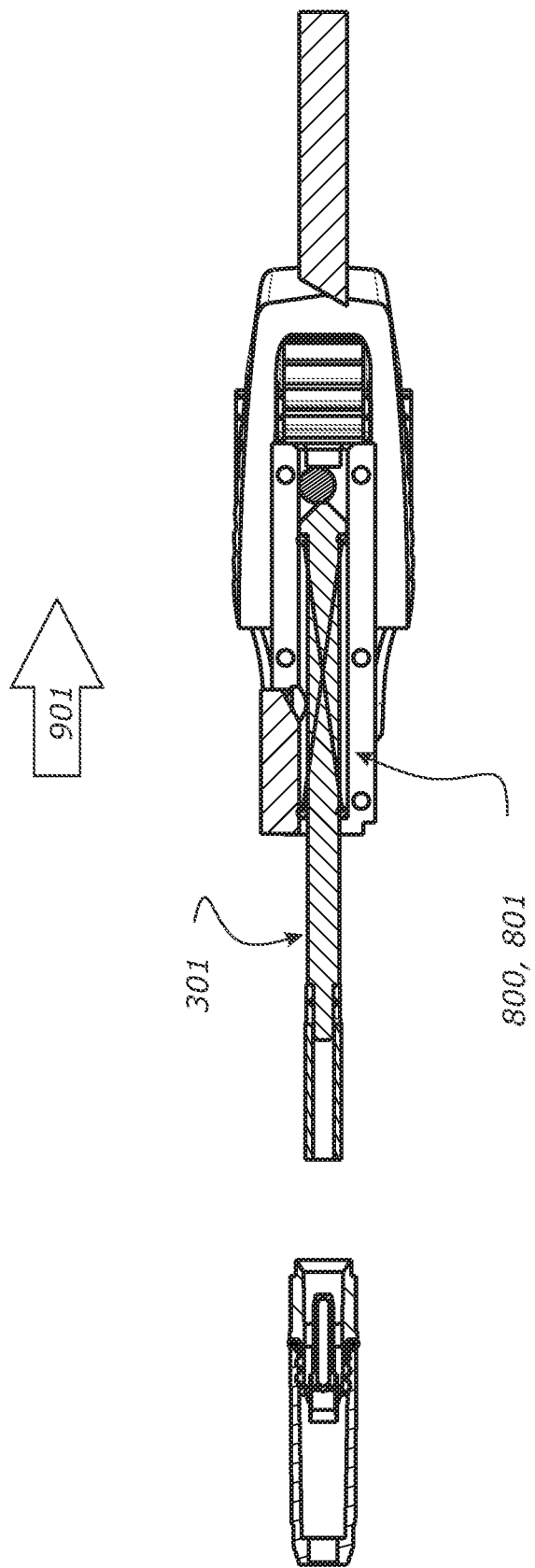
FIG. 11: shows a cross sectional view of the mechanism of FIG. 10 through the plane C-C.

With the release of the coupling 800, the return force of the spring 806 drives the push rod 301 back in the second direction 901 to its retreated position (relative the pushrod driver), while the push rod driver 401 remains at its second position (relative the body 101). This is shown in FIGS. 10 and 11.

If it is desired to repeat the driving stroke and quick release action, the sequence shown in FIGS. 1 to 11 can be repeated, beginning with loading the spring 806 and coupling the push rod 301 and push rod driver 401 by moving the push rod driver 401 in the second direction 901.

In some embodiments the actuator 500 includes a trigger or lever 501, but the actuator 500 could alternatively be a button, switch or rotary knob. An electric motor could be used to drive the drivers. For example, FIGS. 1 to 11 show a trigger or lever 501 which rotates about a pivot point 504 to drive movement of the secondary driver 400 on a rack and pinion 502 via a gear 503. Refer FIG. 6. The gear 503 determines the degree of rotary trigger motion required to drive the secondary driver 400 between its first and second positions. Such an arrangement effects reciprocating motion of the secondary driver 400 in a compact manner.

In some embodiments the arrangement is configured to give a desired travel distance 303 between the operative position of the driven member 200 (which may correspond with or be close to the fully extended position of the primary driver 300 relative the body 101) and the retracted position of the primary driver 300 relative to the body 101. As an example, in some embodiments it may be desired that the distance of travel 303 is between 1 to 500 mm. In some embodiments the distance of travel 303 is between 20 mm to 150 mm, and may be for example between 45 mm-55 mm.

The embodiment described in the drawings shows the primary and secondary drivers 300,400 driving the driven member 200 in a linear motion. A person skilled in the art will appreciate that the arrangement could be adapted for rotary motion of the driven member 200, for example by using curved primary and secondary drivers 300,400 driven in a circumferential or arcuate direction.

A person skilled in the art will understand that the arrangement described is merely an example, and that alternatives could be employed to achieve a similar function. Some specific alternatives are discussed below:

For example, it will be appreciated that many types of releasable coupling 800, other than the detent system described in FIGS. 1 to 11, could be employed. A dog engagement between the secondary driver 400 and primary driver 300 is a preferred form.

As a further example, in a battery powered version of the arrangement previously described in the drawings, the push rod driver 401 could be driven for reciprocation between its first and second positions by an electric motor. The pushrod and pushrod driver could be moved to relative positions where pin engaging apertures are aligned so that the solenoid pin can be inserted to couple them. After the coupled push rod 301 and push rod driver 401 have been driven to their operative positions an electronic trip could withdraw the solenoid pin, releasing the coupling 800 and allowing the retreat of the push rod 301 under the force of a biasing member 805 (which could still be a spring in this example).

As a further example, relative motion between the primary and secondary drivers 300,400 to permit or cause coupling could be effected in different ways. In the embodiment shown in the drawings the secondary driver 400 is moved in the second direction 901 to cause coupling. However, an alternative is that the secondary driver 400 could be moved some distance in the first direction 900 prior to coupling (while compressing the spring 806), or that the primary driver 300 could instead be actuated and moved in the first direction 900.

As a further example, the biasing member 805 could be loaded at different stages of the sequence. In the embodiment shown in the drawings the biasing member 805 is loaded prior to the primary and secondary drivers 300,400 being coupled. However, an alternative is that the biasing member 805 could be loaded as the coupled primary and secondary drivers 300,400 move together in the first direction 900 on the driving stroke, provided that the biasing member 805 is sufficiently loaded before the trip 700 is encountered to release the coupling 800.

An advantage of loading the biasing member 805 prior to commencing the driving stroke is that avoids a loss of driving energy against the resistance of the biasing member 805 being loaded during the driving stroke.

As a further example, FIGS. 1 to 11 show the biasing member 805 carried intermediate of the primary and secondary drivers 300, 400, so as to be loaded by their relative movement and carried with them on the driving stroke. It will be appreciated that the biasing member could alternatively engage with the body 101, and act on one or other (or both) of the primary and secondary drivers 300, 400 to be loaded by virtue of their movement relative to the body 101. For example, the spring 806 could be positioned intermediate the primary driver 300 and a stop or shoulder on the body 101 (stop/shoulder not shown) so as to be compressed as the primary driver 300 moves to its extended position on the driving stroke.

In some embodiments the driven member 200 may have a penetrating element 205 such as a piercing tip or needle to facilitate penetration into the tissue. The driven member may retreat with the primary driver or may push through the tissue and be released from the primary driver.

In one embodiment the driven member is a punch 200 that may have a cutting element 206, such as a cutting edge or blade, which can easily cuts through the tissue. For example the punch 200 shown in FIG. 7 has a circular cutting edge 206.

In some embodiments the punch 200 may be provided as a part of the tool 100, for example, being integral with the primary driver 300. In other embodiments the punch 200 may be provided as an attachment to the tool 100.

For example, in the embodiment shown in FIGS. 1 through 11 the punch 200 is provided as an attachment including a disposable sleeve 208 to engage with the primary driver 300 and to prevent contact between the primary driver 300 and the cutting element. After the punching operation, the sleeve 208 can be removed and discarded to reduce the risk of cross contamination between subsequent tissue samples.

In some embodiments it may be that the driven member 200 retreats from its operative position along with the retreat of the primary driver 300. For example, the driven member 200 may be driven to its operative position, and then retreat with the primary driver 300 withdrawing a plug of tissue or sample of blood or hair or saliva.

However in other embodiments, the driven member 200 may remain at its operative position and dissociate from the primary driver 300 so that the primary driver 300 retreats alone.

For example, in some embodiments the punch 200 may be able to be associated with a container 207 such as a container to collect tissue samples. An example of such an embodiment is shown in FIGS. 1 to 12, wherein the punch 200 associates with a container 207 that is preferably supported by the body 101 of the tool 100 in the line of the driving stroke. The punch 200, when driven in the first direction 900, can penetrate through the tissue to be sampled and be received through an open end of the container 207. The punch 200 may carry the tissue sample into the container 207 with it, and may serve to plug or seal the open end of the container 207 so as to trap the tissue sample within. In these embodiments the punch 200 may remain as a part of the sealed container unit, while the primary driver 300 retreats alone. The entire sealed container unit can then be removed from the tool 100, and a new container 207 and punch 200 installed to collect a subsequent tissue sample.

Figure 12:
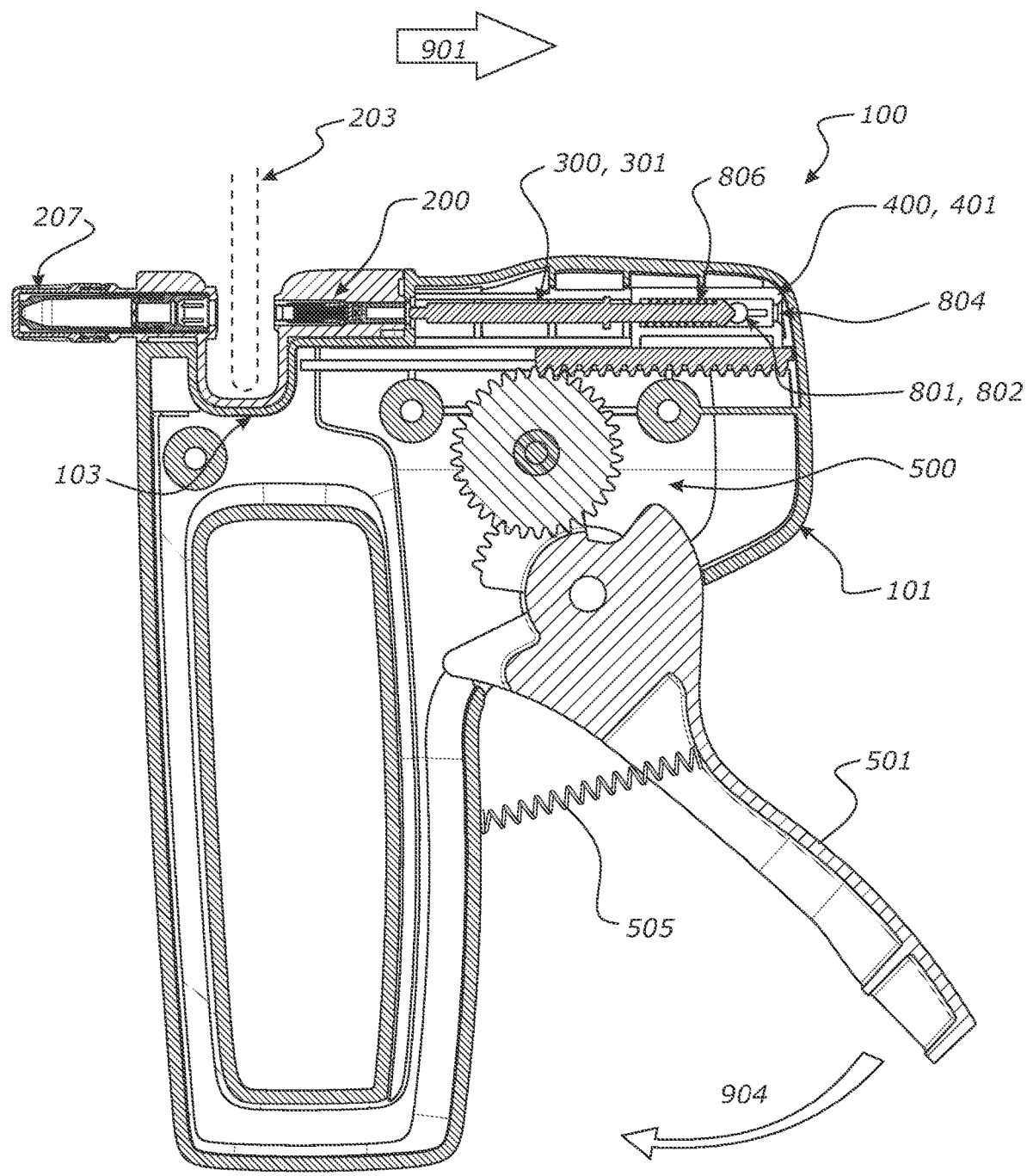
FIG. 12: shows a cross-sectional view of a further embodiment of a quick release driving tool illustrated as a tissue sampler for convenience and with the primary and secondary drivers moved to the retracted positions.

FIG. 12 shows magazine 102 for carrying a series of punches 200 and a series of containers 207 are stored in a rotary magazine 102, by the body 101 of the tool 100. The magazines 102 are rotated to bring both a punch 200 and a container 207 into axial alignment with the primary driver 300, which is initially in its retracted position (relative to the body 101). As the primary driver 300 advances on the driving stroke it drives through the magazine 102 and picks up the punch 200, then continues to drive the punch 200 through the tissue and into the container 207. Once the operative position has been reached (which is in this case the point at which the punch 200 has driven through the tissue and been received by the container 207) the primary driver 300 retreats leaving the punch 200 in the container 207. The magazines 102 are then rotated again to bring a new punch 200 and container 207 into alignment with the primary driver 300 so that a subsequent tissue sample can be collected.

FIGS. 19 to 27 illustrate examples of further embodiments of the invention where an apparatus includes a driving arrangement that operates to carry a driven member such as a punch 200 or assembly that includes a punch 200 to an operative tissue piercing position and to retract as previously described in respect of FIGS. 1 to 11. However in these embodiments the arrangement is configured so that operative tissue piercing position of the primary driver 300 does not correspond with its fully extended position relative the body 101 of the apparatus.

In these embodiments, the primary driver 300:
1. carries the punch 200 in the first direction to or beyond its operative tissue piercing position at some point during the driving stroke (for example the punch 200 may be driven through the item from which the tissue sample is to be taken), and
2. subsequently retreats a distance in the second direction, but then
3. continues to advance in the first direction to its fully extended position (relative to the body 101) to complete the driving stroke.

An advantage of such a configuration is that during a single driving stroke, the primary driver 300 can be used to a) drive the punch 200 for tissue piercing and a quick release from its tissue piercing position, and b) perform a secondary and subsequent driving function that may be useful where a punch as per the punch 604 herein after described with reference to FIGS. 21 to 45 is used.

It will be appreciated that this three-stage movement of the primary driver 300 on the driving stroke could be used to perform a variety of secondary driving functions. As an example of this, the following description explains how the three-stage movement of the primary driver 300 on the driving stroke can be used to a) drive a punch 200 to obtain a tissue sample and b1) insert an end cap to close a tissue sample container and/or b2) cause a plunger associated with the punch to be actuated to cause the sample to be removed from the punch.

FIGS. 19 to 22 show a first embodiment of a hand-held tool 100 including a mechanism by which such a three-stage movement can be achieved. FIGS. 16 to 20 show an alternate mechanism by which such a three-stage movement can be achieved.

Following that there is description of a sampling collecting assembly 601 (comprising a punch 604 (also herein designated 200)) and sample storage container 602 which can be used in conjunction with the hand-held tool 100 and any one of the mechanisms described herein.

Reference is now to FIGS. 12 to 15, to explain the parts and operation of a quick release tool 100 for collecting tissue samples such as from an ear 203 of an animal, where the ear is to be positioned in a slot 103 of the apparatus prior to sampling. Initially this positions the ear 203 intermediate of a punch 200 held at one side of the slot 103, and a sample container 207 held at the opposite side of the slot 103.

The tool may have an actuator 500 that includes a lever 501 carried by the body 101 of the tool 100. The lever 501 may be biased toward an open condition as shown in FIG. 12 by a lever biasing member 505. A user of the device may rotate the lever 501 against the bias in the direction shown as 904 in FIG. 12, for example by squeezing the lever over one in the palm of their hand. Rotating the lever 501 towards a closed condition, as shown in FIG. 15, will effect a driving stroke of the punch 200.

Rotation of the lever 501 acts via a gear 503 to cause linear movement of a secondary driver 400. In this embodiment this secondary driver is a push rod driver 401, which drives a pushrod three (the primary driver) that carries the punch 200.

Figure 15:
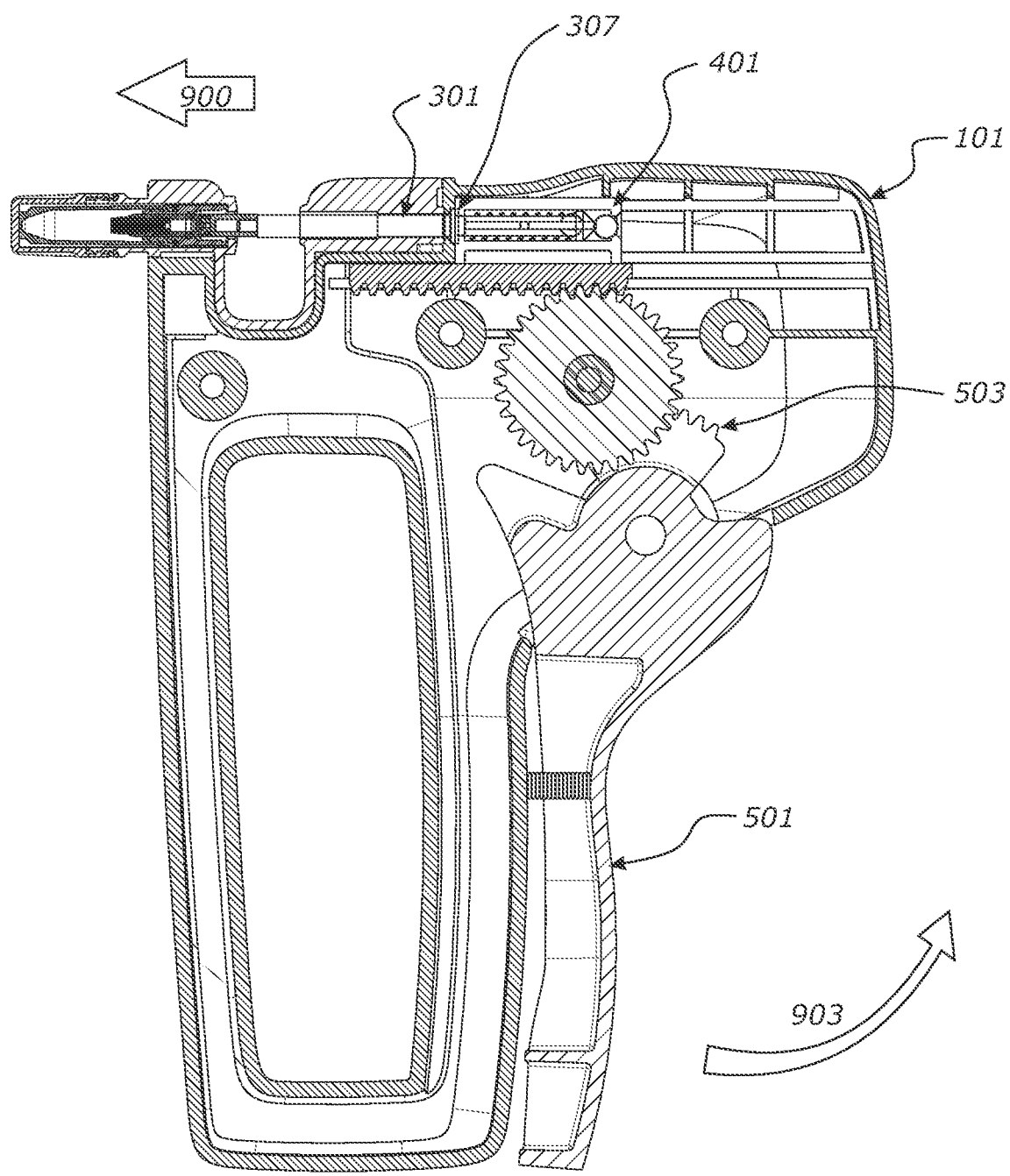
FIG. 15: shows the sampler of FIG. 12 with the primary and secondary drivers being driven together to the end of the driving stroke, reliant on a secondary coupling between them having been established.

The push rod is driven between a retracted position (relative to the body 101) which can be seen in FIG. 12 and an extended position (relative to the body 101) which can be seen in FIG. 15. Similarly, the push rod driver 401 reciprocates between a first position (relative to the body 101) shown in FIG. 12 and a second extended position (relative to the body 101) shown in FIG. 15.

Relative movements of the push rod 301 and push rod driver 401 in order to effect the driving stroke of the punch 200 are shown in sequence in the FIGS. 12 to 15. In the following description the direction of the driving stroke, shown by arrow 900 in the Figures, is referred to as the first direction 900. The opposite direction, shown by arrow 901 in the Figures, is referred to as the second direction 901.

The sequence begins as shown in FIG. 12 with the push rod driver 401 being moved in the second direction 901 toward its first retreated position, as will tend to occur under the bias of the lever biasing member 505. Because the push rod 301 is coupled to the push rod driver 401 by a spring 806, this movement will draw the push rod 301 into its retracted position. As the push rod driver 401 continues to move in the second direction 901, the corresponding movement of the push rod 301 in the second direction 901 is limited by a stop 804. Thus there may be relative movement of the push rod 301 and driver 401 which compresses the spring 806 between them.

As the push rod driver 401 reaches its first retreated position, the push rod and push rod driver are coupled together by a detent 801. The detent engagement relies upon a ball 802 intermediate of the push rod end 301 and the stop 804 being displaced radially outward of the push rod axis, guided on the stop 804. The ball 802 is displaced into a corresponding recess 803 of the push rod driver 401. Thus the push rod 301 is coupled to the pushrod driver 401 with the push rod 301 in a primed position (relative the driver), and the coupling 800 also holding the spring 806 in its compressed condition.

Figure 13:
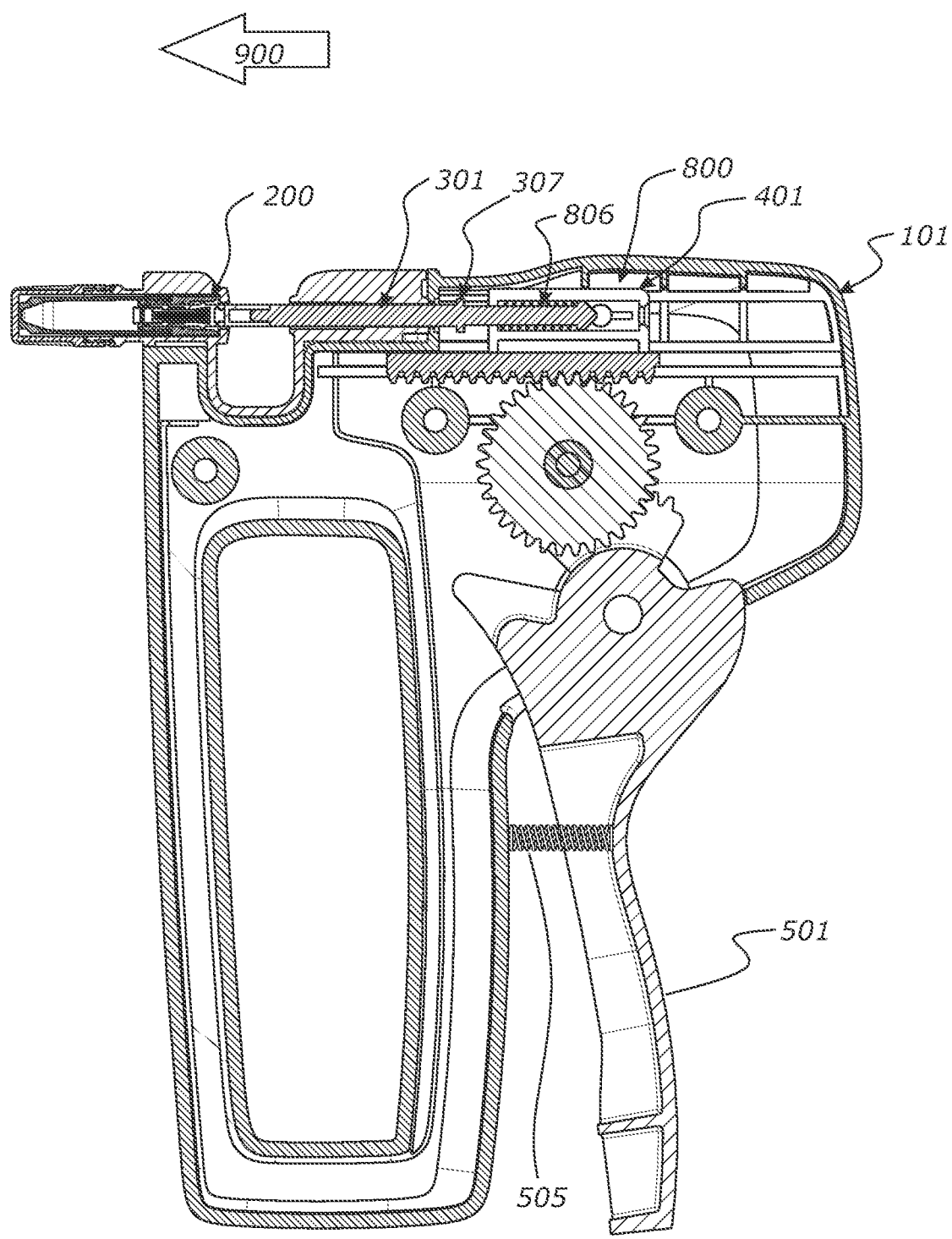
FIG. 13: shows the sampler of FIG. 12 with the secondary driver being driven towards its extended position, and a punch being driven through the operative piercing position by the primary driver.

As shown in FIG. 13 the actuator 500 is engaged to drive the coupled push rod 301 and push rod driver 401 in the first direction 900, carrying the compressed spring 806 with them. In this condition, the push rod 301 drives the punch 200 to its operative tissue piercing position (which is in this case the point at which the punch 200 has driven through the ear of the animal and been received by the container 207).

However at this point the push rod 301 has not yet reached its fully extended position (relative the body 101), nor has the push rod driver 401 reached its second position.

As the push rod driver 401 advances toward its second position (relative the body 101), the coupled drivers encounter the trip 700, which is in this case a camming surface 701 (for example that which can be seen in FIG. 8). Movement of the coupled drivers in the first direction 900 relative to the camming surface 701 causes the detent ball 802 to be guided or displaced radially inward to release the coupling 800.

Figure 14:
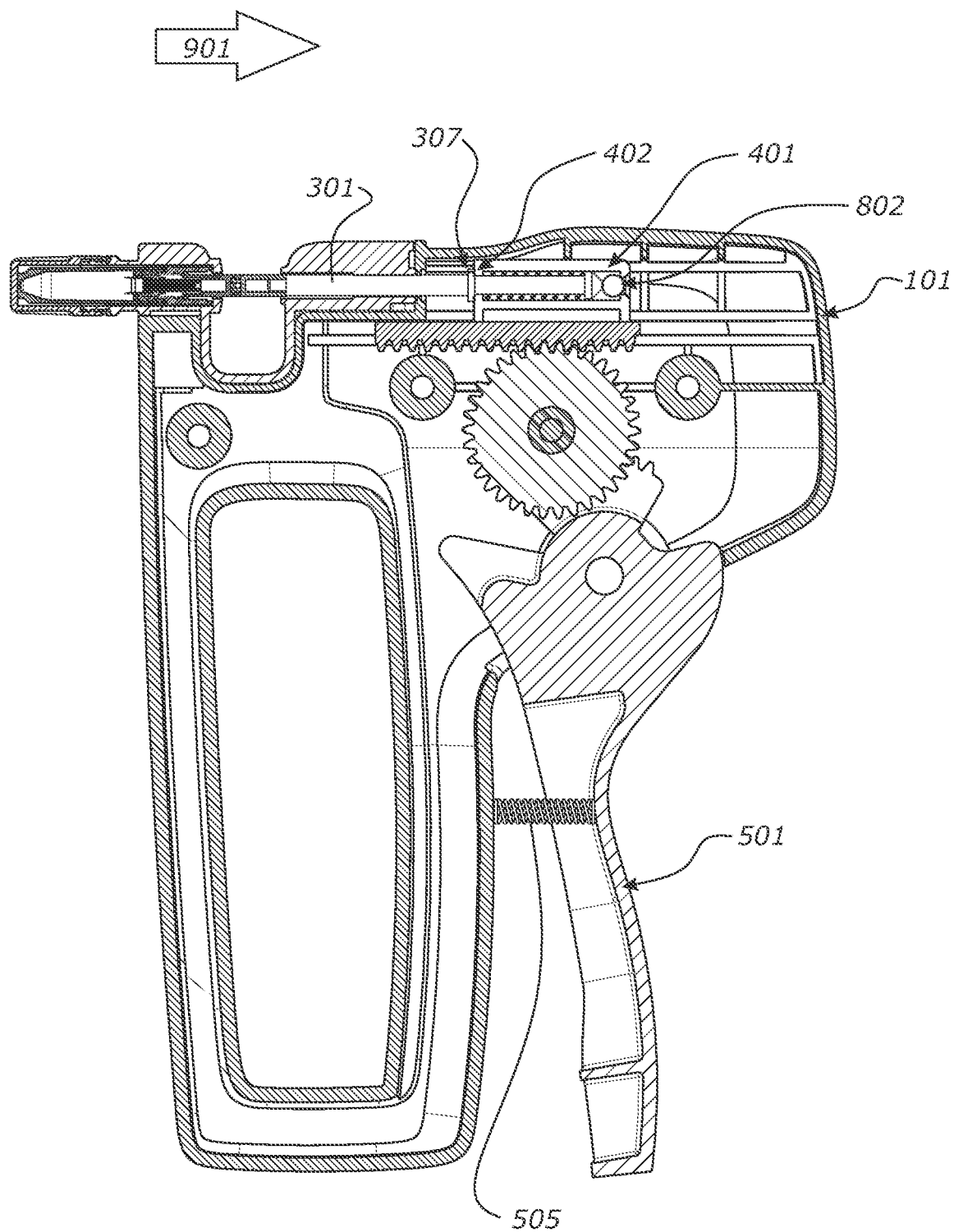
FIG. 14: shows sampler of FIG. 12 with the primary and secondary drivers have been momentarily decoupled to permit the primary driver to retreat.

With the release of the coupling 800, the return force of the spring 806 drives the push rod 301 back in the second direction 901 to a retreated position (relative the pushrod driver), while the push rod driver 401 remains at its second position (relative the body 101). This is shown in FIG. 14.

Subsequent to this momentary decoupling of the push rod 301 and push rod driver 401, and the retreat of the push rod 301 under the bias of the spring 806, a secondary coupling between push rod 301 and the push rod driver 401 is established. For example, there may be surface to surface contact which engages them, or selective engagement of a dog. In the embodiment shown in FIGS. 12 to 15 the engagement is between a shoulder 307 of the push rod and an end surface 402 of the push rod driver 401. The push rod driver 401 is brought into contact with the shoulder 307 as the push rod moves 301 back in the second direction 901.

The push rod driver 401 is able to push on the shoulder 307 to drive the push rod 301 so that both continue together in the first direction 900 until the push rod 301 has reached its limit of extension, and thus the driving stroke is complete.

After completion of the driving stroke, both the push rod 301 and push rod driver 401 may be returned to their respective starting positions under the bias of the lever-mounted spring 505. It will be noted that alternative means could be employed to bias the push rod driver (and/or the push rod) toward their starting positions. For example, the teeth of the gear 503 could disengage at the end of the driving stroke so as to allow a spring acting between the body 101 of the apparatus and the push rod driver 401 to return the driver to its first position. In further embodiments there may not be a bias, so that manual rotation of the lever and the direction of arrow 903 is required to reset the mechanism.

Referring now to FIGS. 16 to 20, the mechanism for a three stage movement of the primary driver 300 may include primary and secondary driver 400s as previously described, however and this embodiment the primary driver 300 itself comprises two relatively movable parts: a tertiary driver 305, and a quaternary driver 306.

The tertiary driver 305 may be a push rod 301 which provides, carries or connects to the punch. The tertiary driver 305 may slide in a telescoping manner with in the quaternary driver 306.

The tertiary and quaternary drivers can be selectively coupled in order to move together. The features of the coupling between the tertiary and quaternary drivers may be essentially the same as described in respect of the primary and secondary drivers, there being a spring 806 and a detent 801 engagement which operate all as previously described in respect of the primary and secondary drivers. These can be seen in the Figures. Not visible from the Figures, but present, is the trip 700 surface which can be encountered firstly by the coupled tertiary and quaternary drivers, and subsequently by the coupled primary and secondary drivers in order to sequentially release the couplings between them as previously described in respect of the preceding embodiments.

Figure 16:
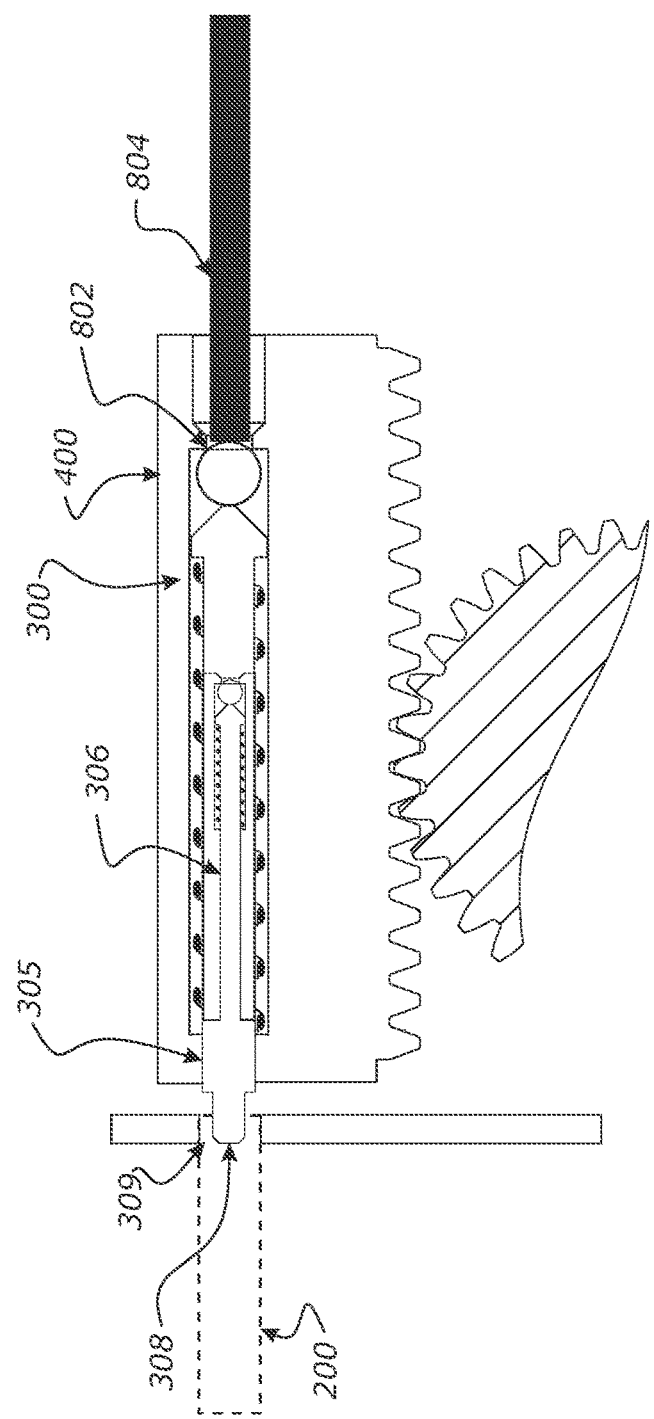
FIG. 16: shows, in cross-section, an alternative mechanism to be used in the sampler of FIG. 12, with the primary driver (which comprises a tertiary and a quaternary driver) in its retracted position but prior to the springs of the mechanism having been loaded.
Figure 20:
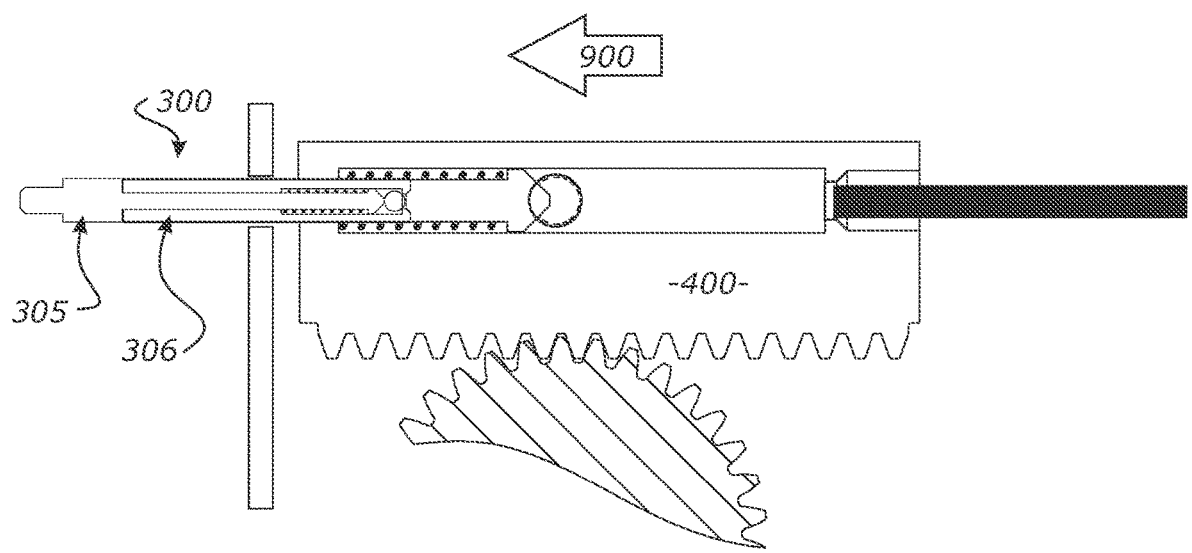
FIG. 20: shows the mechanism of FIG. 17 where there has been a continued driving of the primary and secondary members to the limit of the driving stroke.

The primary driver 300 is driven between a retracted position (relative to the body 101) which can be seen in FIG. 16 and an extended position (relative to the body 101) which can be seen in FIG. 20. Similarly, the secondary driver 400 reciprocates between a first position (relative to the body 101) shown in FIG. 17 and a second extended position (relative to the body 101) shown in FIG. 20.

Figure 17:
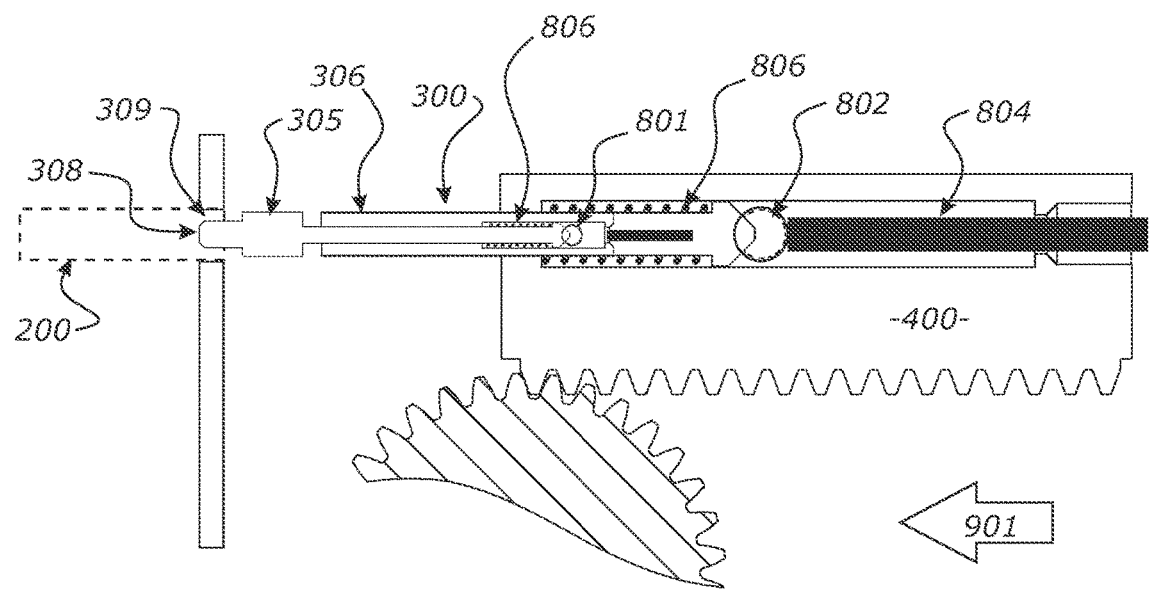
FIG. 17: Shows mechanism of FIG. 17 with the secondary driver has been retracted to its first position, thus loading the springs of the mechanism, coupling the drivers, and forcing the tertiary driver to its extended position.

The tertiary driver 305 is moveable between a retracted position (relative to the quaternary driver 306) which can be seen in FIG. 16 and an extended position (relative to the quaternary driver 306) which can be seen in FIG. 17.

Relative movements of the drivers in order to effect the driving stroke of the punch 200 are shown in sequence in the FIGS. 16 to 20. In the following description the direction of the driving stroke, shown by arrow 900 in the Figures, is referred to as the first direction 900. The opposite direction, shown by arrow 901 in the Figures, is referred to as the second direction 901.

FIG. 23 shows the mechanism prior to either of the biasing members 806 being loaded, with the secondary driver 400 in its second position, and the primary driver 300 retreated with respect to the secondary driver 400 and at the limit of its retraction with respect to the body 101. The tertiary driver 305 is retracted with respect to the quaternary driver 306.

The sequence begins with movement of the secondary driver 400 in the second direction 901 towards its first retreated position as shown in FIG. 17. Movement of the primary driver 300 is limited by the stop 804. Thus there is relative movement between the primary and secondary drivers which compresses the spring 806.

Figure 24:
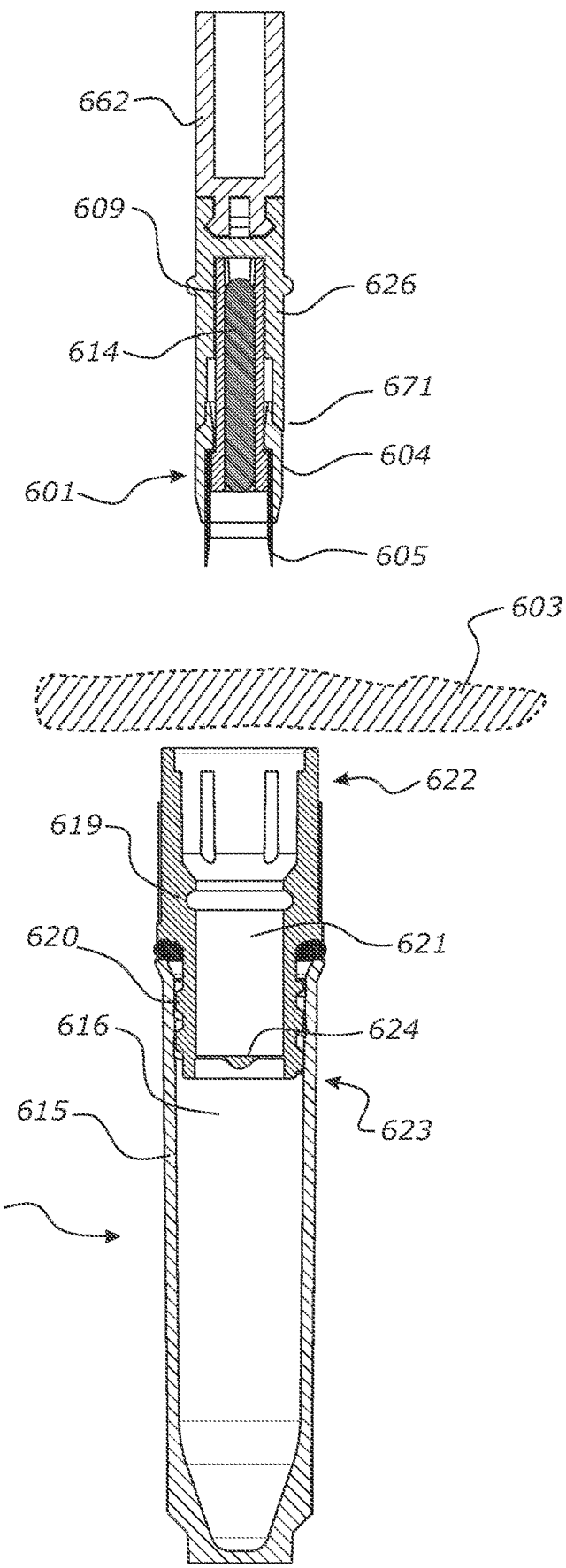
FIG. 24 is a perspective view of the storage container and sample collector/sample collector driver/push rod string intermediate of which for example a part of an ear of an animal is placed prior to sampling.

The end 308 of the tertiary driver is preferably retained in place while the secondary driver 400 moves in the second direction 901 as can be seen in FIGS. 16 and 24. For example, where the tertiary driver end 308 is engaged with a punch 200, the punch may push fit into the aperture 309 and this can serve to hold the driver end 308 in place until the driving stroke begins. As the quaternary driver 306 moves back in the second direction 901 with the secondary driver 400, it can be seen that the stationary tertiary driver 305 is drawn to its extended position (relative the quaternary driver 306).

As the secondary driver 400 reaches its first retreated position, the secondary and primary drivers are coupled together by a detent 801, as are the tertiary and quaternary drivers. The detent 801 engagement between the primary and secondary drivers relies upon a ball 802 intermediate of the driver end and the stop 804 being displaced radially outward of the driver axes, guided by the stop 804. The detent 801 engagement between the tertiary and quaternary drivers relies upon a ball 802 being displaced radially outward, for example under a magnetic force, into a corresponding recess. The detent couplings 801 also hold the springs 806 in a compressed condition.

Figure 18:
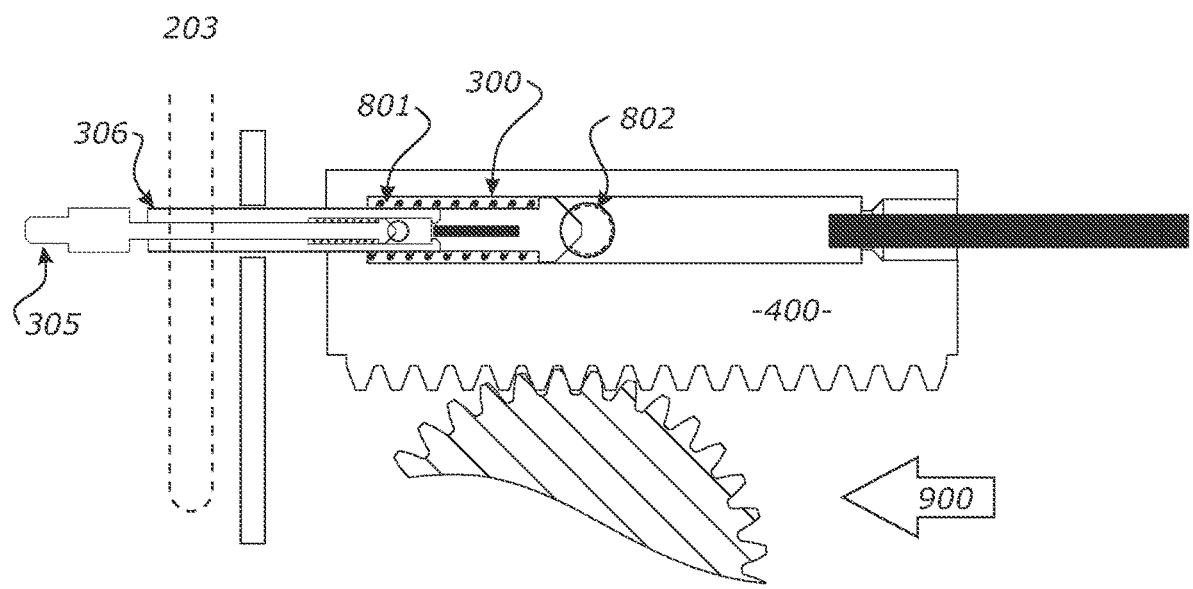
FIG. 18: shows the mechanism of FIG. 17 where the coupled primary and secondary drivers have commenced the driving stroke and have driven the punch through for example the ear of an animal to collect a tissue sample.
Figure 19:
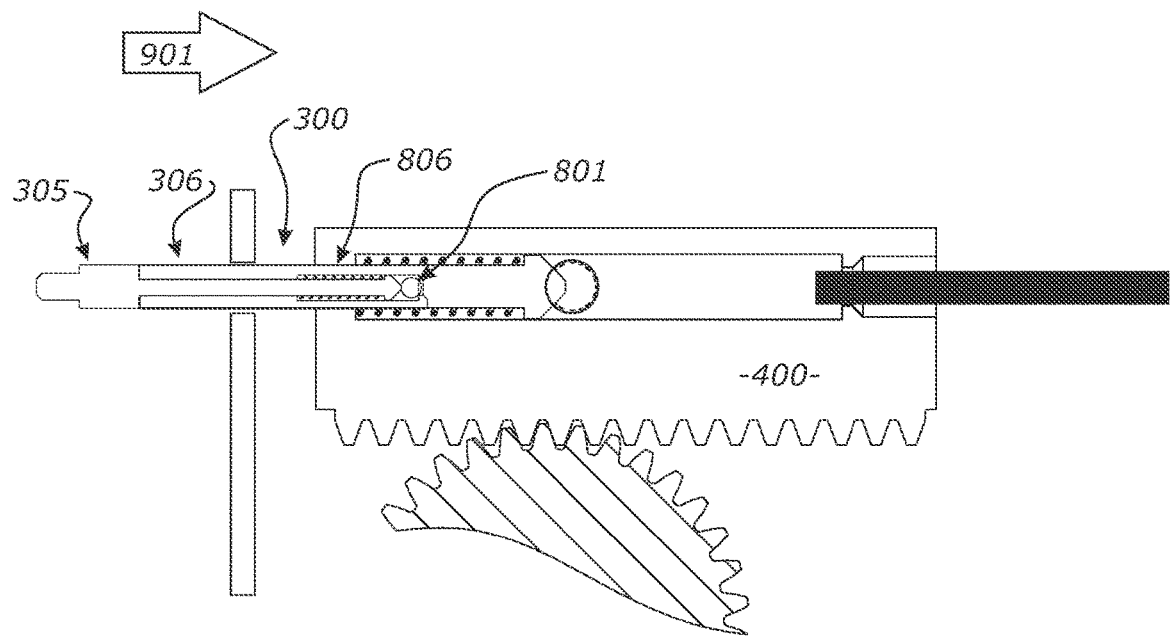
FIG. 19: shows the mechanism of FIG. 17 where there has been a retreat of the tertiary driver.

The actuator 500 is engaged to drive the coupled drivers in the first direction 90, carrying the compressed springs 806 with them. In this condition, the punch 200 is driven through the ear 203 of the animal in order to collect a tissue sample as shown in FIG. 18. However at this point the primary driver 300 has not yet reached its fully extended position (relative the body), nor has the secondary driver 400 reached its second position. When the tertiary and quaternary drivers encounter the trip 700, the ball 802 is guided inwardly, overcoming the magnetic force, in order to release the coupling. The tertiary driver retracts back in the second direction 901 under the force of spring 806.

The secondary driver continues to travel in the first direction 900. As the secondary driver 400 advances toward and/or reaches its second position (relative the body 101), the primary driver 300 is driven to the limit of its extension and thus the driving stroke is completed. However at this point the coupled primary and secondary drivers encounter the trip 700. The detent 801 coupling is disengaged by the trip, and the primary driver 300 retreats to its retracted position (relative the body) under the bias of the spring 806.

In this embodiment there is an immediate retreat of the primary driver 300 to its retracted position at the end of the driving stroke so as to render it clear of the ear of the animal as quickly as possible.

As previously discussed, either mechanism (as shown in FIGS. 12 to 15, or as shown in FIGS. 16 to 20) can be used to effect a three-stage movement of the primary member. It will now be described how such a three stage movement can be used to drive a punch associated with a sample collecting assembly, so that the collected sample can be inserted in a sample storage container and a cap of the storage container can be applied.

The sample collecting assembly that include the punch is as shown in FIGS. 21 to 45. It is intended that the sample collecting assembly could engage with the end of the primary driver 300 and be driven thereby.

With reference to FIGS. 21 to 45 a sample collector 601 with a punch, and storage container 602 is shown. As seen in FIG. 21 a sample storage container 602 is shown that includes a container body 615 that has a containment region 616 that is terminated by an end wall 618 and a side wall 617 and includes a cap 619.

In the preferred form the end wall 618 of the containment region 616 is closed and not openable. It may alternatively be openable. In the preferred form the side and end walls are integrally formed. The container body 615 is preferably made from a plastics material. It may be a moulded plastics material. A preservative may be provided inside of the containment region 616.

The storage container 602 can receive a sample collector retained sample. Prior to receiving a sample the containment region 616 is preferably sealed. In the preferred form the storage container 602 also includes an end at where the sample collector penetrates the storage container, preferably in the form of a cap 619 that is either integrally formed with or secured and preferably removably secured to the container body 615. The cap 619 receives the sample collector 601 upon the taking of a sample such as from an animal's ear.

The cap 619 is preferably threadingly engaged to the container body 615 by virtue of threads 620. The cap can be screwed onto and preferably partially ascend into the container body 615. It can be unscrewed from the container body to gain access to the containment region. This may occur in a laboratory to gain access to the sample in the containment region.

In the preferred form the cap has a passage 621 that has an entrance 622 and an end 623 opposed at the entrance 22. The passage 621 is of a shape and configuration to be able to snugly receive the sample collector 601. It is preferably cylindrical in shape. In the preferred form the side walls of the passage 621 correspond substantially to an exterior side wall of the punch 604. Such an exterior side wall is preferably round in cross sectional shape. Preferably no gap or passage exists between the cap and the sample collector when the sample collector is located in the passage. This helps seal the storage region 616.

Within the passage and preferably at the end 623 opposed the entrance, the passage is sealed by a frangible seal 624. This could also be a plug or a membrane. The frangible seal 624, when the cap 619 is secured to the container body 615 and prior to the sample collector being received, seals the containment region 616 of the container body. The frangible seal 624 is preferably frangeably attached so that when a sample collector is delivered into the passage 621 it is able to push against the seal 624 to at least partially separate the seal 624 and allow for the sample to be pushed into the storage region 16. In the preferred form the sample is still retained in the bore 608 at the cutting end of the punch 604 when the frangible seal is at least partially separated to open the storage region 616.

The cap preferably has an additional function and/or feature to help seal the containment region that will herein be described.

The sample storage container 602 is able to receive the sample collector 601 also shown in FIG. 21.

The sample collector 601 includes at a cutting end 606, a cutter 605 associated with or part of a punch 604.

The sample collector 601 shown in FIG. 24 is in a pre-sampling condition relative to the organism 603 to be sampled and the storage container 2, aligned with the storage container 602 intermediate of which for example a part of an animal's ear 603 is positioned.

The sample collector 601 comprises a punch 604 having a body with a cutter 605 presenting a cutting end 606 that is able to penetrate into the organism to be sampled.

The cutter 605 is provided at a first end of the punch 604. The punch has an opposing driving end 607. It is at the driving end that the punch can for example be driven by the primary drive or quaternary driver as has herein before been described for purposes of pushing the cutting end (and preferably the entire collector) at least partially into and preferably all the way through the organism to be sampled to take a sample. In the preferred form the entire sample collector 601 is ultimately pushed through the tissue to be sampled.

The body of the punch 604 preferably has a bore 608. The bore 608 extends from one end of the punch 604 to the other. It preferably extends along the length of the punch 604 between the cutting end 606 and the driving end 607. Preferably the punch 604 is an elongate straight body and the bore is centrally located within the punch. The cutter 605 defines at least part of this bore. The bore is preferably circular in cross section.

In the preferred form as can be seen in FIG. 22, the cutter 605 preferably has a circular cutting end. Preferably the cutter is substantially cylindrical shaped. It will be appreciated that alternative shapes can be used. It may be 3 or more sided for example.

The cutter 605 is provided at the cutting end of the punch to facilitate removal of a sample from an organism. The cutter may be attached to the punch or it may be integral with the punch so that the cutter and the punch are formed as a single part. It need not be formed to take a core sample by pushing through the organism but a sample instead taken at an edge of surface of the organism. However, being of a hollow section such as a cylindrical section offers the added benefit of the cutter being able to retain the sample as a plug. When driven into and preferably through an organism the sample becomes retained at the bore 608 of the punch. The cutter 605 preferably extends from and surrounds one end of the bore 608 of the punch at the cutting end of the punch.

In the form shown in FIGS. 21 and 22, the bore 608 is effectively a blind bore by virtue of the provision of a plunger 609 being located in the bore of the punch 604. The plunger 609 is aligned with the bore. The plunger 609 is held at the bore 608 of the punch to form part of the sample collector 601. In one form the plunger protrudes at least partially from the bore 4. The plunger and the punch in a pre-sampling condition are configured so that a cavity, extending inwards from the cutting end 608 and that is part of the bore, is provided for a sample to be collected in as the sample collector 601 is driven into and/or through the organism.

Figures 37, 38, 39:
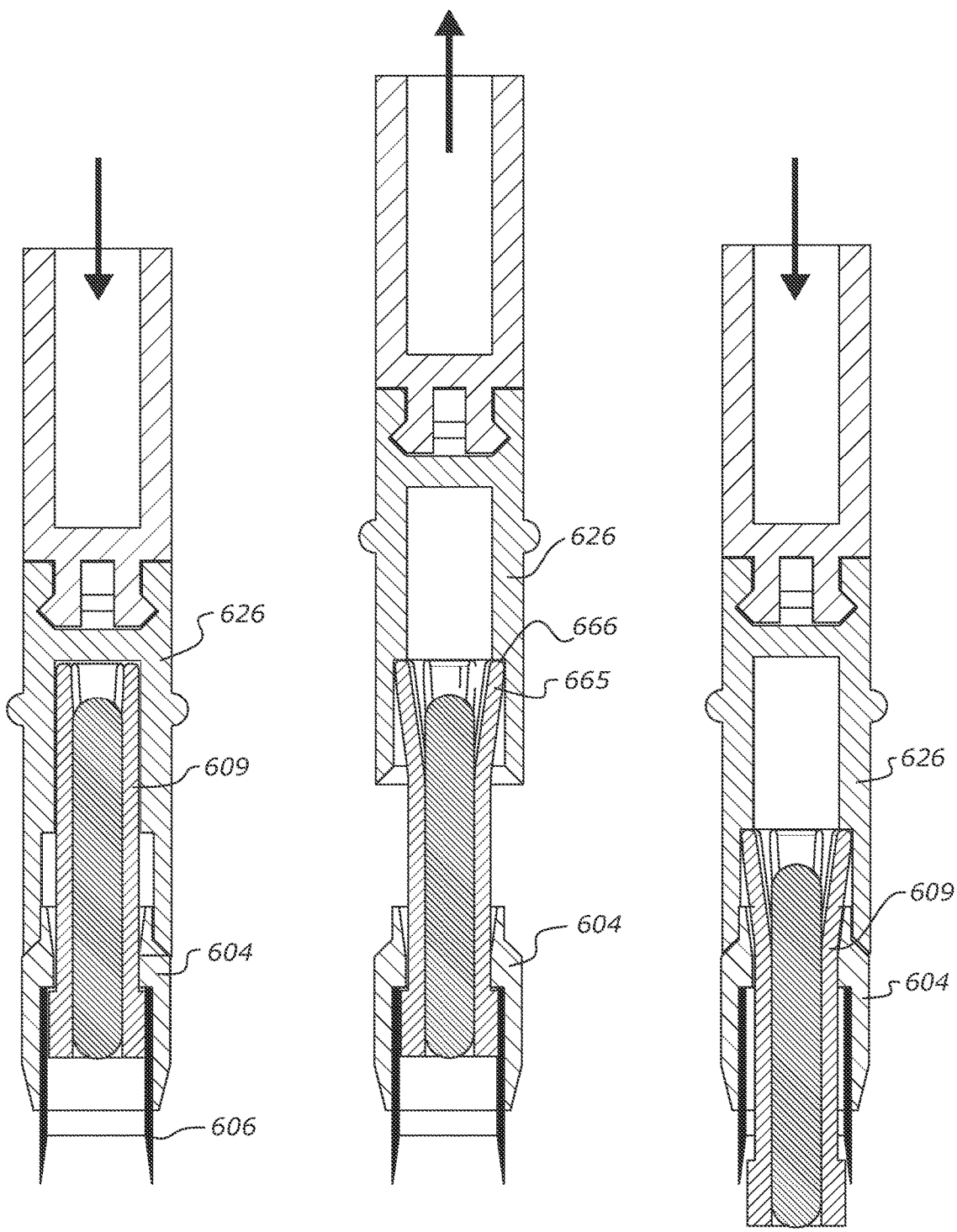
FIG. 37 is an enlarged view of the string of components including the sample collector, the tool driver and the push rod wherein these components are in a condition to for example punch through the ear of an animal.
FIG. 38 shows the components of FIG. 37 but wherein the tool driver has telescopically moved relative to the sample collector and to its expanded position relative thereto in order to ratchet with the plunger for the purposes of then re-advancing for the purposes of driving a plunger relative to the punch as can be seen in FIG. 46.
FIG. 39 shows the plunger having been moved to its advanced position relative to the punch by a re-advancement of the sample collector driver.

The plunger has a first end 687 and a second end 666. The first end is a pushing end to push onto the sample to push it out of the cavity. The second end is the driving end to drive the plunger in a manner that will herein after be described. The fit of the plunger 609 in the bore 608 is snug yet allowing for the plunger to be slid relative to the punch. In the preferred form the plunger's outer surface is contiguous the inner surface of the bore. This ensures that a close fitting configuration is provided between the punch 604 and the plunger 609 thereby helping to prevent the ingress of contaminants from the driving end of the punch to or towards the cutting end of the punch through the bore. The plunger and the punch are in a slidable relationship with each other. They are in a slidable relationship with each other so that a sample, once collected from the organism and retained in the bore at and near the cutting end 606 can be ejected therefrom by the plunger 609. Preferably the first end is able to be pushed all the way to the cutting end 606 to thereby eject the sample collected from the sample collector. Actuation of the plunger may be by pushing at the first end 10 of the plunger. The plunger is able to be positioned in an active position as shown in FIG. 37 and be moved to a plunged position as shown in FIG. 39 in a manner herein described.

Preferably the plunger 609 includes an enlarged region 613 that prevents the plunger from being pulled out of the punch 604 from the driving end 607. The enlargement and a corresponding constriction in the bore of the punch limit the movement of the plunger and it cannot be removed by pulling the plunger out of the punch from the driving end 607. This helps prevent external access being gained to the sample once collected and it held at the cavity or dispensed further into the containment region 616 of the storage container.

In the preferred form the actuation of the plunger causes the sample to eject from the bore and into the containment region 616.

The plunger 609 preferably includes an EID tag 614.

The plunger as has hereinbefore been described, can move axially along the bore of the punch to allow for the sample that is collected by the cutter 605 to be pushed from the collector and into the containment region 616 of the storage container 602. The plunger includes a pushing end 687 that is able to push the sample from the cutter and it includes a driving end 666.

At the driving end opposite the cutting end, the sample collector 601 is preferably able to be pushed to be displaced by a sampler device through for example the ear of an animal in order to cause the sample to be collected.

The sample collector 601 is associated with a tool driver 626 during the process of sampling. The sample collector and tool driver may be assembled as an elongate string. In use, the tool driver first pushes the sample collector through the ear of an animal. It can then be caused to push the plunger to dispense the sample into a containment region and then optionally to seal the containment region. This will now be described.

The tool driver 626 is provided for sampling, connected to the sampler collector, as is for example seen in FIGS. 24 and 25. The form of the connected tool driver and sample collector is such that the components are axially aligned and resemble an elongate (preferably straight) string akin to a drill string, along the aligned axis.

In the preferred form a push rod 662 is removably connected to the tool driver 626 during the process of sampling. The push rod 662 is optionally provided for the purposes of driving the sample collector and the tool driver through the ear of an animal and provides an extension or a sleeve about the driving rod of the sampler device 1300. This helps to avoid cross contamination of samples during the sampling process. The push rod 662, once sampling has occurred, is able to be removed from the tool driver 626. As can be seen in FIG. 23*a* an interference fit plug 667 is provided. The interference fit plug 667 is able to locate in a socket 668 at an end of the tool driver 626 but is able to be removed therefrom upon the application of a sufficient force. The assembly of the sample collector 601 and the tool driver 626 and optionally where included the push rod 662 are substantially of a slender elongate configuration that is substantially of a constant diameter or other external profile. This helps ensures that the assembly is able to be pushed through the ear of an animal to collect a sample. As can be seen the sample collector and tool driver and push rod, are preferably elongate and straight and serially connected as in a drill string. They are preferably axially aligned.

The push rod 662 as seen in FIG. 23*a* is preferably of a configuration to act as a sleeve for the actuator driver of the sampler device. A cavity 669 is provided into which the actuator driver can locate to then drive the assembly of the sample collector, the tool driver and the push rod by pushing on the end wall 670 of the push rod 662.

The plunger 609 has a telescoping relationship with the tool driver 626 such that the plunger and the tool driver may move between a first and second position relative to each other. Facilitated by the telescoping relationship the plunger and tool driver may be engaged in a ratchet-like connection. The ratchet-like connection acts to allow movement in one telescoping direction but then to prevent motion or to prevent motion past a certain point in the opposite direction. The ratchet-like connection may be in the form of a dog or umbrella like formation 665 or other physical obstruction or engagement provided by either the plunger or tool driver or by provided an interaction of both the plunger and sample collector driver.

Several examples of possible ratchet-like connections are shown in FIGS. 31*b-j*. In the preferred embodiment the plunger may include a driving end 666 that is defined by an umbrella 665. The umbrella is naturally biased to an expanded condition as shown in FIG. 34 but can be caused/forced to assume a contracted condition as seen in FIG. 33.

The relationship between the tool driver 626 and the punch 604 and the plunger 609 is such that the three components are able to axially displace relative to each other. This will now be described. The sample collector and tool driver and storage container are able, for the purposes of sampling, to be held by a sampler device 1300.

In a first condition (the punching condition) as seen in FIG. 25 the tool driver 626 is engaged with the punch 604 at an interface 671 so that a force applied by the actuator mechanism of the sample device 1300 via the push rod 662 pushing onto the tool driver 626 can push the punch 604. The punch 604 and the tool driver 626 are in a compact position relative each other for the purposes of such pushing to drive the sample collector and the tool driver through the ear of an animal. The punch and plunger are in a retracted position relative each other so that a cavity is defined by the cutter and the plunger to allow a sample to be collected and held in the cavity. The plunger and the tool driver are in a first position where the plunger is located in the cavity 672 of the sample collector driver. The umbrella of the plunger is in a contracted condition. So in the first condition the:

1. Tool driver and punch are in a compact position,
2. Punch and plunger are in a retracted position, and
3. Plunger and tool driver are in a first position with the umbrella in the contracted condition.

The sample collector and preferably also the tool driver are, in this first condition, able to be driven through the ear of the animal and engaged with the storage container as seen in FIG. 26.

In a second condition, after the cutter has passed through the ear of the animal and a sample is held in the cavity, as seen in FIG. 29, the plunger 609 remains in a retracted position relative to the punch 604. The punch is snugly held by the cap of the storage container and tool driver is moved back towards where it came from by the mechanism of the sampler device. The tool driver and punch, in the second condition are in an expanded position relative each other. They are preferably telescopically engaged. The punch and plunger remain in a retracted position but the plunger and tool driver are in a second position relative each other where the umbrella is in an expanded condition and no longer in the cavity 672.

So in the second condition the:

1. Tool driver and punch are in an expanded position having been so configured due to the stutter mechanism of the sampler device herein before described,
2. Punch and plunger are in a retracted position, and
3. Plunger and tool driver are in a second position with the umbrella in the expanded condition.

In a third condition as seen in FIG. 35 the tool driver is pushed back towards the punch and preferably back to or near its earlier compact position. This is achieved by the driving mechanism of the sampler device that will herein after be described. In the third condition, the plunger has moved to an advanced position relative the punch. The tool driver and plunger remain in the second position with the umbrella in the expanded condition. The tool driver is also now fully seated with the storage container at the cap where it may seal the storage container.

So in the third condition the:

1. Tool driver and punch are in or near the compact position,
2. Punch and plunger are in an advanced position, by virtue of the secondary driver or quaternary driver re-advancing after the intermediate decoupling, and
3. Plunger and tool driver are in a second position with the umbrella in the expanded condition.

The opposite distal end of the plunger includes an umbrella 665 that is in a contracted condition when the punch and the tool driver are in the compact position. The umbrella is retained in a contracted condition by virtue of being in a first cavity 672 of the tool driver 626. The first cavity 672 is of a nature that will hold the umbrella 665 of the plunger 609 in a contracted condition as seen in FIG. 23b. In the preferred form the driving end 666 of the plunger is located against the end wall 673 of the first cavity 672. The plunger 609 extends from the first cavity through a second cavity 674 from the tool driver 626. Preferably the first cavity 672 is a bore of a first diameter. The second cavity 674 is preferably a bore of a larger diameter and includes an end wall 675 with which the driving end 666 of the plunger can engage when the plunger has been axially displaced relative the tool driver 626 and out of the first cavity 672. Upon a displacement the umbrella 665 which is naturally biased to an expanded condition, is able to expand and upon such expansion is then not able to re-enter the first cavity 672. Instead the driving end 666 is able to contact the end wall 675 of the second cavity 674. When in the axially displaced condition relative to the tool driver 626 further driving of the tool driver 626 towards the storage container will result in the plunger being displaced relative the punch. This occurs by virtue of the interaction of the driving end 666 with the end wall 675 of the second cavity.

The umbrella 665 is preferably integrally formed as part of the plunger 609. The plunger and its umbrella is preferably of a plastics material and the umbrella is preferably naturally formed in an expanded condition but is of a configuration that allows for it to be collapsed to a contracted condition as seen in FIG. 23b.

As can be seen in FIGS. 25 and 26 when the sample collector and tool driver are being driven into the ear of the animal the sample collector and tool driver are in a compact position and a driving of the punch occurs by the interface between the tool driver and the punch. In FIG. 26 it can be seen that a sample 612 has been removed and is held by the cutter 605. The plunger is still in a retracted position relative to the cutter and has not been moved to eject the sample from the cutter 605.

The storage container 602 and preferably its cap 619 is able to snugly receive the punch 604 and be guided for a sliding movement into the bore of the cap 619. The assembly of the sample collector and tool driver is able to be driven through the ear of the animal as seen in FIG. 27. As previously described, the axial relationship between the punch and the tool driver and the plunger remains the same at this stage of sampling as before the sample was taken. The assembly of the tool driver and the sample collector is merely displaced through the ear of the animal and has engaged with the cap of the storage container 2. The sample collector is able to advance in the bore of the cap in order to reach the flangible seal. This seal is preferably of a configuration as hereinbefore described. The punch can push onto, to remove the flangible seal 624.

Preferably once the frangible seal 624 has been broken (but alternatively prior to this point) the axial relationship between the tool driver 626 and the sample collector 601 is changed. The tool driver 626 is retracted at least partially back towards where it came from and moves at least partially back out of the cap as seen in FIG. 3. The mechanism of the sampling device may cause this displacement. The sample collector 601 (the punch 604 and plunger 609) remain in its position relative to the storage container where it was delivered by the sampler device and does not retract back with the tool driver 626. The partial retraction of the tool driver 626 causes a relative axial displacement of a distance sufficient to allow for the driving end 666 of the plunger 609 to displace out of the first cavity 672 of the tool driver 626. This causes the umbrella to expand. Preferably the retraction distance is substantially no greater than that required for the driving end 666 to move out of the first cavity 672 and allow for the umbrella to expand. The umbrella in its expanded condition is now able to engage the end wall 675 of the second cavity 674 of the tool driver 626.

As seen in FIGS. 30 and 31a, the size or shape $d_1$ of the driving end 666 of the plunger is approximately the same as the size $d_2$ of the cavity 672 of the sample collector driver. This is when the punch is in its compact position relative to the tool driver and the plunger is the first position relative to the sample collector driver. In the second position of the plunger relative to the sample collector driver, the size or shape $D_1$ of the driving end corresponds to the size or shape $D_2$ of the second cavity of the sample collector driver.

Further displacement of the tool driver 626 into the cap causes the tool driver 626 to drive the plunger 609 and thereby will eject the sample 612 from the cutter 605 as seen in FIG. 32.

A continued advancement of the tool driver 626 as can be seen in FIG. 35 will cause the tool driver 626 to lodge into the passage of the cap and thereby provide an additional seal to the containment region. The tool driver 626 may include an enlargement 676 that is able to push into an annular recess 677 of the bore of the cap. The interaction of the enlargement and the annular recess can provide further barrier to the ingress or egress of contaminants and/or sample material to and from the storage region 616 of the storage container 602. The interaction of the enlargement and the annular recess will also help hold the tool driver in a fixed relationship to the cap so that a retraction force applied to the push rod 662 will cause the release of the push rod 662 from the tool driver 626 as can be seen in FIG. 36.

As can be seen in the sequence of images of FIG. 37-39 in a first condition as seen in FIG. 37 the tool driver 626 and punch 604 are in a compact relationship relative to each other and the plunger 609 is in a retracted position relative to the punch 604. This is the punch mode of the assembly. In FIG. 38, the punch and tool driver are in their expanded position relative to each other, where the tool driver 626 has been retracted away from the punch 604 to allow for the umbrella 665 to expand and for the driving end 666 to contact the end wall 675 of the sample collector driver. An advancement of the tool driver 626 back towards the punch 604 will then cause the plunger 609 to displace relative to the punch 604 to its advanced position and for the sample to be ejected. The displacement back towards the punch 604 will also displace the tool driver 626 further into the cap than it was when it was in a punch condition as seen in FIG. 37 so that the tool driver 626 can fully seal the bore of the cap.

In alternative forms the tool driver may be removed from the sample collector after it has driven the sample collector into the storage container and has actuated the plunger. The tool driver may not seal the storage container. The tool driver maybe disposed.

FIGS. 38*b-j* show variations to the telescopic ratchet relationship of the plunger and the sample collector driver. FIGS. 31 *c, e, g* and *i* shows the driver and plunger in where the relationship between the two, when assembled would be where the plunger is in the retracted position and figures d,f,h,j respectively shows the driver and plunger in where the relationship between the two, when assembled would be where the plunger is in the advanced position.

Figure 40:
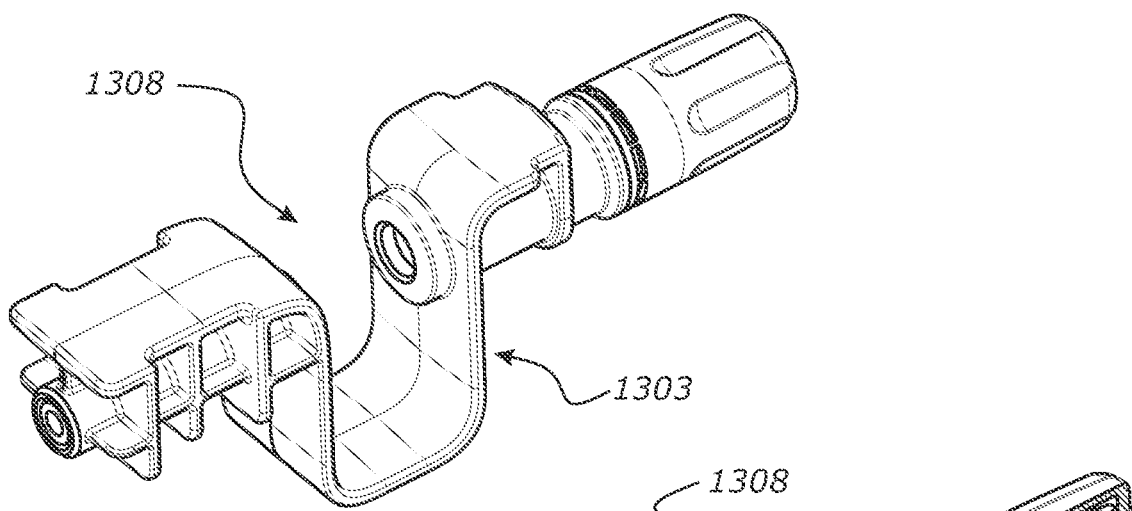
FIG. 40 shows an assembly of the storage container and the string of components including the sample collector and tool driver associated with a cartridge, the cartridge being able to be delivered to an end user with the sample collector related string and storage container in pre-alignment with the gap between at where the ear of an animal may be placed.
Figure 41:
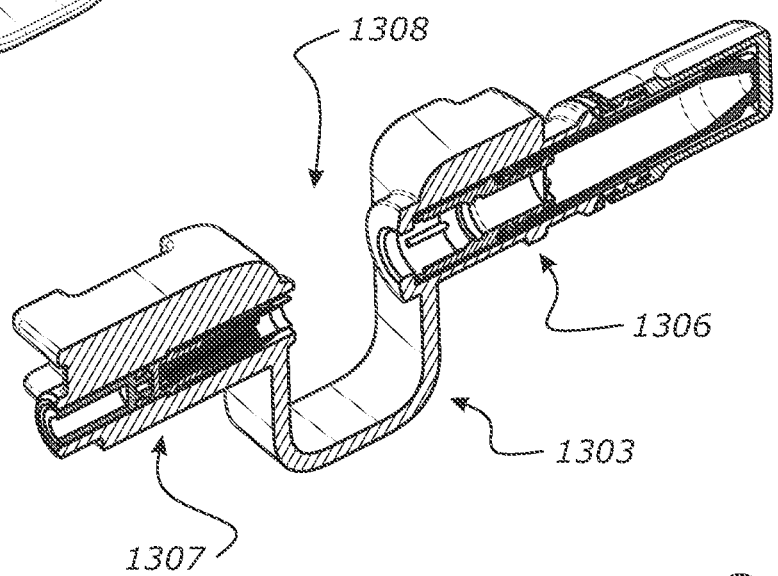
FIG. 41 is a cross sectional perspective view of FIG. 40.
Figure 42:
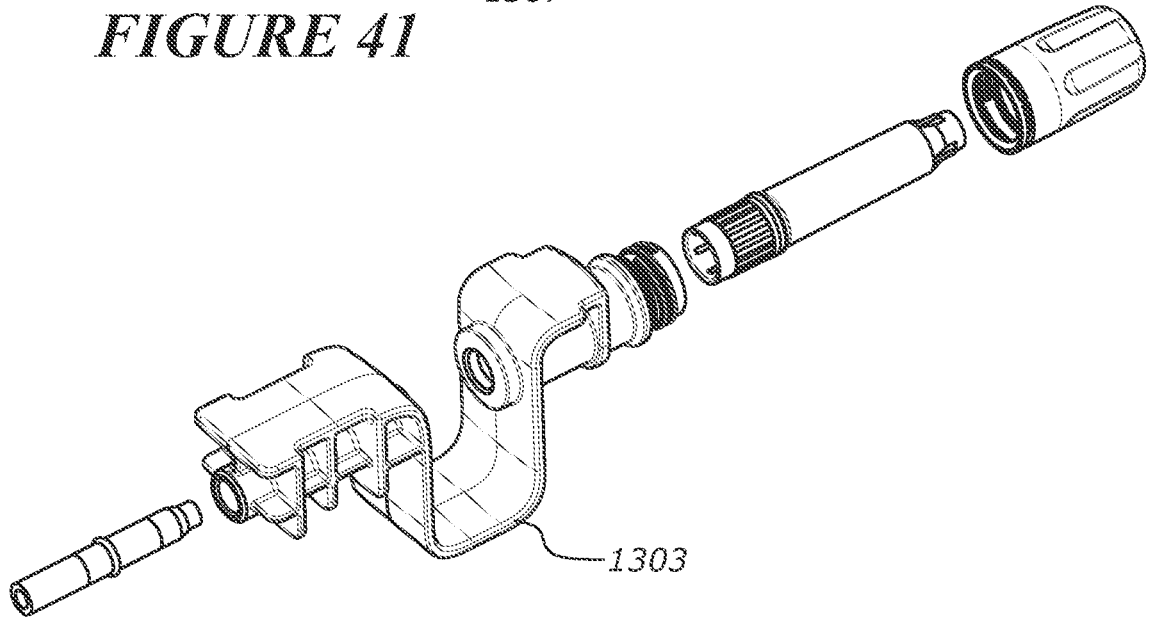
FIG. 42 shows a partially expanded view of the components of FIG. 40.
Figure 43:
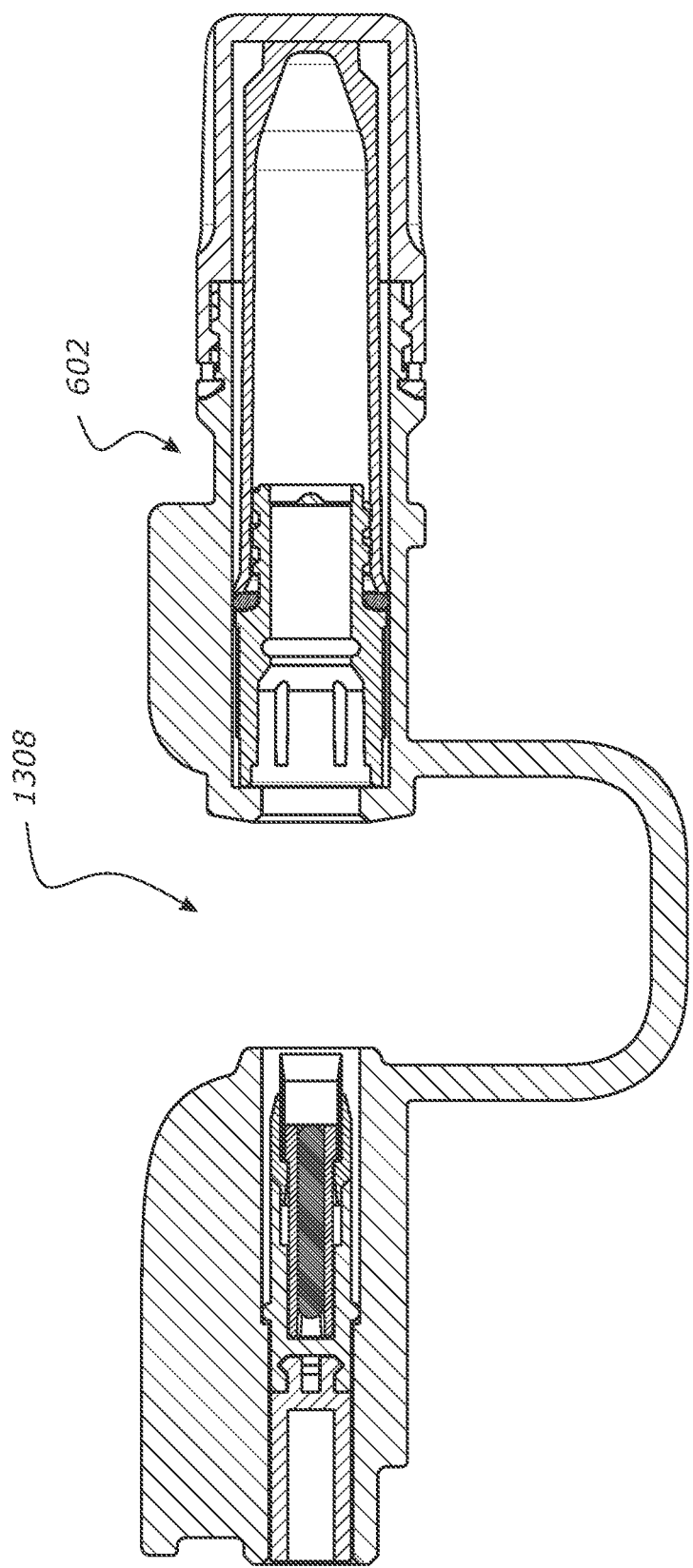
FIG. 43 shows a cross sectional view of the components of FIG. 40.
Figure 44:
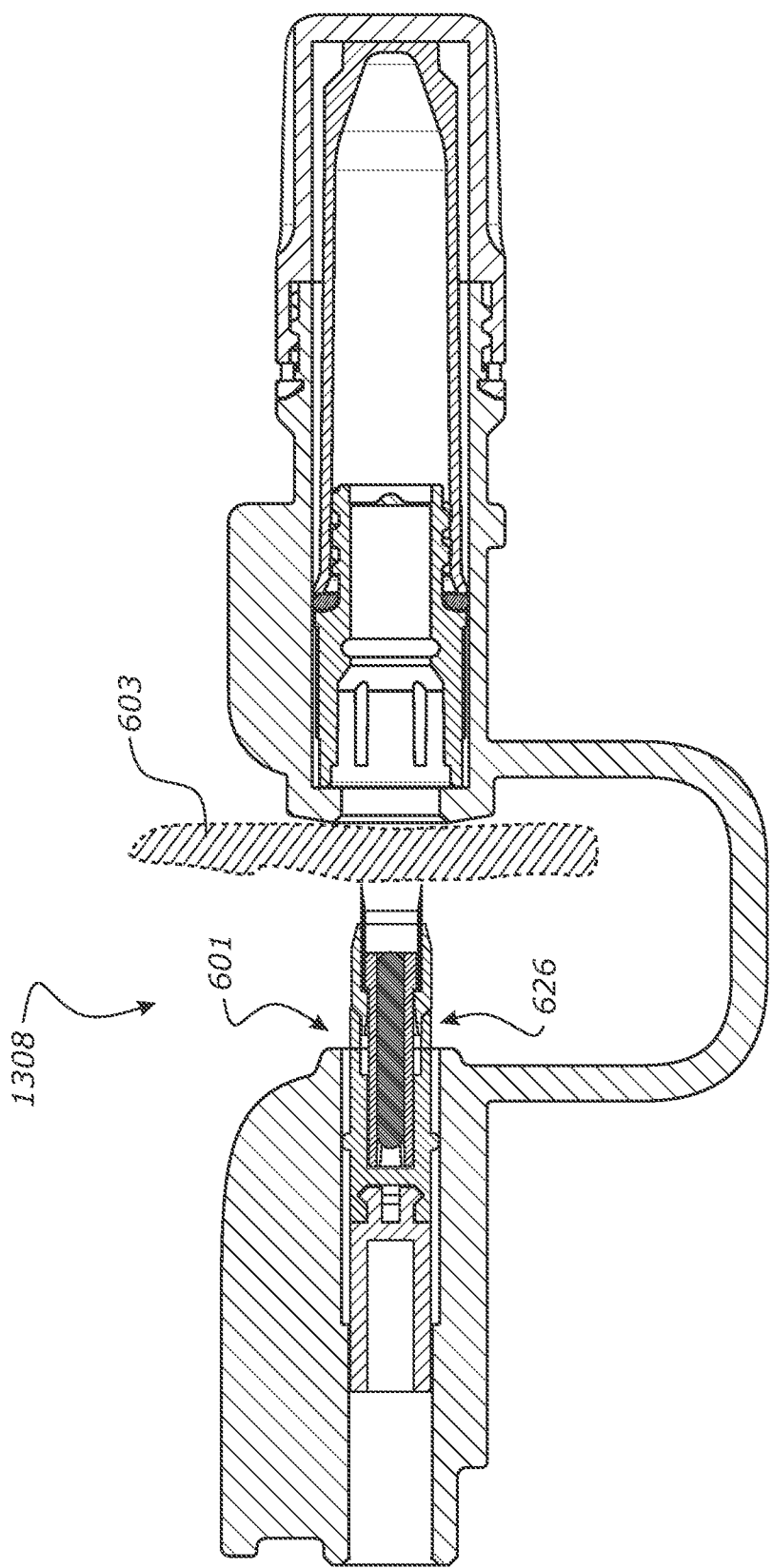
FIG. 44 shows a cross sectional view of the components of FIG. 40 but wherein the string of components including the sample collector is advanced towards the storage container immediately prior to the taking of a sample from the ear of an animal.

The sample collector and tool driver and the storage container may be provided in a form associated with a cartridge 1303. The cartridge may be a body that defines a storage container holding region 1306 and a sample collector and tool driver holding region 1307 as seen in FIGS. 40 and 41. An exploded view of this is shown in FIG. 43. The body of the cartridge 1303 holds the sample collector and storage container and tool driver in an axially aligned condition. It holds the storage container in a condition separated by a gap 1308 from the sample collector. As seen in FIG. 44, the gap 1308 is sufficiently large to allow for an ear 630 of an animal to be inserted into the gap and be presented to be axially aligned for the purposes of taking the sample. The cartridge 1303 is able to be loaded into a sampler device herein before described. It is preferably able to be removably loaded so that once the sample has been taken, the cartridge can be removed. Upon removal the storage container may remain associated with the cartridge and be shipped as a unit to a laboratory for further processing.

Figure 45:
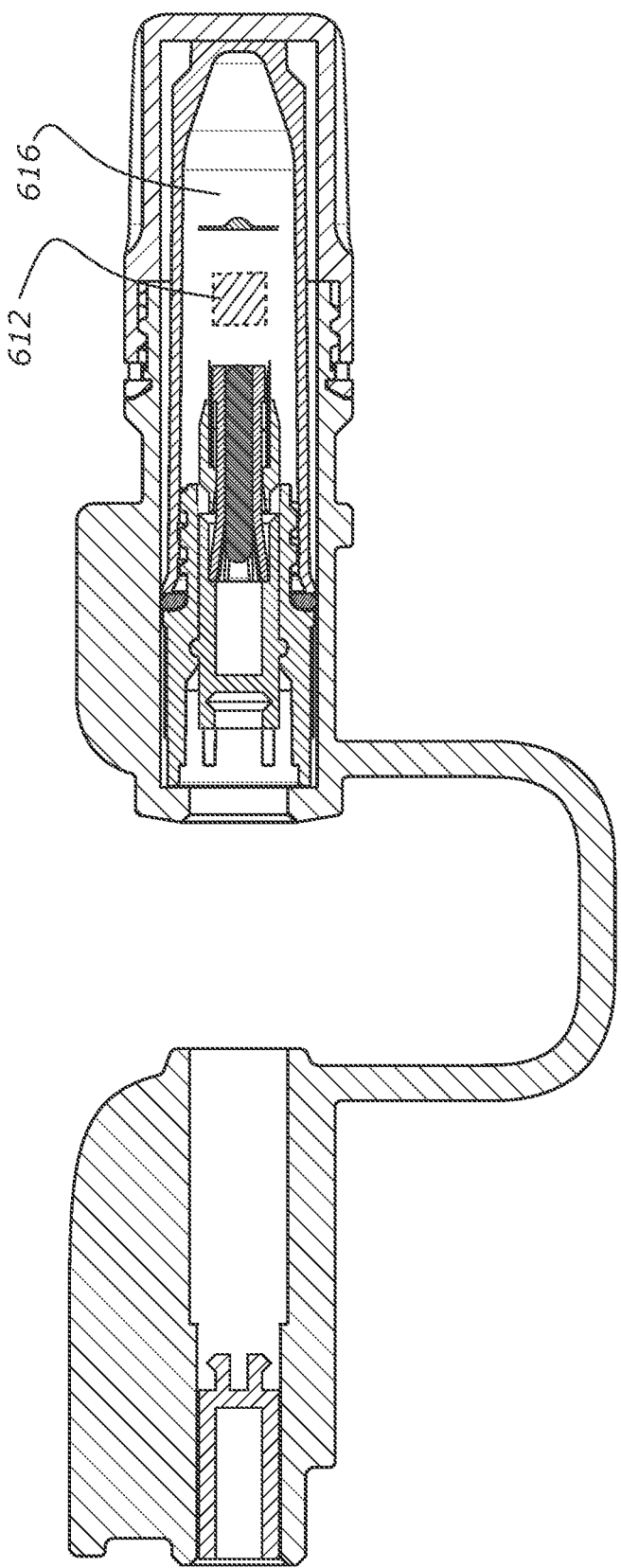
FIG. 45 shows the storage container having received the sample and the sample collector having sealed the storage container.

A cross-sectional view of the arrangement of FIG. 41 is shown in FIG. 43. This is the pre-sampling condition where the tool driver and sample collector 601 are on one side of the gap 1308 and the storage container 602 is on the opposite side of the gap. FIG. 44 shows the sample collector 601 and tool driver 626 assembly being delivered for taking a sample of the ear 603 of an animal. FIG. 45 shows the sample collector and tool driver having been delivered to the sample collector, the tool driver 626 sealing the cap of the sample collector and the plunger having been actuated to push the sample 612 into the storage region 616.

The cartridge 1303 is able to be removably associated with the sampler device. In a removed condition shown the cartridge 1303 with the sample collector, tool driver and storage container pre-associated therewith, (preferably at the factory and prior to delivery of the end point of use), is able to be inserted into the sampler device. After sampling the cartridge may be removed from the sampler device with the storage container still engaged and carrying the sample collector and sample and may then be shipped to a lab. Where in the foregoing description reference has been made to elements or integers having known equivalents, then such equivalents are included as if they were individually set forth.

Although the invention has been described by way of example and with reference to particular embodiments, it is to be understood that modifications and/or improvements may be made without departing from the scope or spirit of the invention.

The invention claimed is:

1. A device to cause tissue of an animal to be penetrated by a punch, said device comprising:
    a body,
    a push rod that includes a punch end or that can carry a separate punch from, relative to said body, a retracted position to an extended position where the punch at least partially penetrates the tissue,
    a push rod driver that is mounted to said body, displaceable relative to said body in a first direction by an actuator mounted to said body at least from a first position to a second position, said push rod slideably mounted to said push rod driver to move relative thereto in the first direction between a primed position and a retreated position,
    a dog, selectively operable between the push rod and push rod driver, that:
        connects said push rod and said push rod driver so that movement of said push rod driver in the first direction can impart movement of said push rod to its extended position,
        is tripped when the push rod reaches its extended position to release the push rod from its primed position and cause the push rod to slide in a second direction, being a direction opposite the first direction, towards its retracted position under the influence of a bias,
    wherein the push rod and push rod driver are able to move relative to each other by linearly telescoping one inside the other, and the dog is contained internal of the push rod and push rod driver in their linearly telescoping relationship.

2. The device as claimed in claim 1, wherein the dog comprises a ball selectively engageable with a detent of one or both of the push rod or push rod driver.

3. The device as claimed in claim 2, wherein the ball may be selectively engaged solely by movement of the push rod driver relative to the push rod.

4. The device as claimed in claim 2, wherein the body comprises a stop at one end of the push rod driver opposite the push rod, and selective operation of the ball into engagement with the detent is provided by the bias of the push rod acting against the ball which is consequently forced against the stop of the body.

5. The device as claimed in claim 4, wherein the engagement of the ball with the detent occurs under a sliding of the push rod driver in the second direction relative to the push rod the stop of the body.

6. The device as claimed in claim 4, wherein the bias of the ball towards an engaged condition is due to
   a) the action of the push rod under its bias towards the stop of the body, and
   b) a configuration of surfaces adjacent the ball of either or both the push rod and stop of the body.

7. The device as claimed in claim 1 wherein the push rod driver is, after retreat of the push rod relative to the extended position, again able to be driven in the first direction and drive the push rod in the first direction relative to the body to complete a driving stroke of the push rod.

8. The device as claimed in claim 1 wherein the push rod and the push rod driver are adapted and configured to engage each other upon movement of a secondary driver in the first direction and after tripping of the dog.

9. The device as claimed in claim 8 wherein one or the other of the push rod and the push rod driver has an outwardly projecting shoulder, wherein engagement with each other upon movement of the push rod driver in the first direction and after the tripping of the dog occurs by virtue of interference between the shoulder of one of the push rod and the push rod driver and a surface of the other of the push rod and the push rod driver.

10. The device as claimed in claim 9 wherein each of the push rod and the push rod driver has an outwardly projecting shoulder, wherein engagement with each other upon movement of the push rod driver in the first direction and after tripping of the dog occurs by virtue of interference between the shoulders.

* * * * *